(12) United States Patent
Conboy et al.

(10) Patent No.: US 11,573,233 B2
(45) Date of Patent: Feb. 7, 2023

(54) SYSTEMS AND METHODS FOR LABEL-FREE DETECTION OF ANALYTES

(71) Applicant: UNIVERSITY OF UTAH RESEARCH FOUNDATION, Salt Lake City, UT (US)

(72) Inventors: John Conboy, Salt Lake City, UT (US); Krystal Sly, San Diego, CA (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 471 days.

(21) Appl. No.: 15/280,212

(22) Filed: Sep. 29, 2016

(65) Prior Publication Data

US 2017/0089908 A1 Mar. 30, 2017

Related U.S. Application Data

(60) Provisional application No. 62/284,412, filed on Sep. 29, 2015.

(51) Int. Cl.
*G01N 33/543* (2006.01)
*G01N 33/574* (2006.01)
(Continued)

(52) U.S. Cl.
CPC ..... *G01N 33/57484* (2013.01); *G01N 21/636* (2013.01); *G01N 33/543* (2013.01); *G01N 21/05* (2013.01)

(58) Field of Classification Search
CPC ........... G01N 33/543; G01N 33/57484; G01N 21/636; G01N 21/05
See application file for complete search history.

(56) References Cited

U.S. PATENT DOCUMENTS

| 5,767,971 A | * | 6/1998 | Kawai | G01N 21/45 356/517 |
| 2002/0127563 A1 | * | 9/2002 | Salafsky | B82Y 30/00 435/6.12 |

(Continued)

FOREIGN PATENT DOCUMENTS

EP 0740156 * 4/1996

OTHER PUBLICATIONS

Nguyen et al., Comparioson of the Energetics of Avidin, Streptavidin, NeutrAvidin and Anti-Biotin Antibody Binding to Biotinylated Lipid Bilayer Examined by Second-Harmonic Generation, Nov. 2011, Analytical Chemistry, vol. 84, pp. 201-208. (Year: 2011).*

(Continued)

*Primary Examiner* — Melanie Brown
(74) *Attorney, Agent, or Firm* — Ballard Spahr LLP

(57) ABSTRACT

Disclosed are methods of detecting an analyte of interest comprising introducing a sample comprising an analyte of interest to an antibody or antibody fragment; incubating the sample and antibody or antibody fragment under conditions sufficient to allow binding of the analyte of interest to the antibody or antibody fragment; and detecting the binding of the analyte of interest to the antibody or antibody fragment using a label-free second harmonic detection system. Also disclosed are methods of screening and diagnosing using antibodies or antibody fragments and a label-free second harmonic detection system.

11 Claims, 12 Drawing Sheets

(51) Int. Cl.
    G01N 21/63    (2006.01)
    G01N 21/05    (2006.01)

(56) References Cited

U.S. PATENT DOCUMENTS

| | | | | |
|---|---|---|---|---|
| 2005/0118731 A1* | 6/2005 | Salafsky | ............... | B82Y 30/00 |
| | | | | 436/518 |
| 2006/0291772 A1* | 12/2006 | Haiml | ............... | G01N 21/6428 |
| | | | | 385/16 |
| 2010/0177307 A1* | 7/2010 | Rimke | ............... | G01J 3/44 |
| | | | | 356/301 |
| 2011/0236998 A1* | 9/2011 | Liscidini | ............... | G01N 21/648 |
| | | | | 436/518 |
| 2011/0267617 A1* | 11/2011 | Carney | ............... | G01N 21/636 |
| | | | | 356/341 |
| 2012/0202296 A1* | 8/2012 | Eisenthal | ............... | G01N 21/636 |
| | | | | 436/501 |
| 2014/0248709 A1* | 9/2014 | Eisenthal | ............... | G01N 21/636 |
| | | | | 436/501 |

OTHER PUBLICATIONS

Smith KA, Gale BK, Conboy JC. Micropatterned Fluid Lipid Bilayer Arrays Created Using a Continuous Flow Microspotter. Analytical Chemistry 2008;80:7980-7.

Nguyen TT, Rembert K, Conboy JC. Label-Free Detection of Drug-Membrane Association Using Ultraviolet-Visible Sum-Frequency Generation. Journal of the American Chemical Society. 2009;131:1401-3.

Stokes G, Conboy John C. Measuring Selective Estrogen Receptor Modulator (SERM)—Membrane Interactions with Second Harmonic Generation. Journal of the American Chemical Society. 2014;136:1409-1417.

Nguyen TT, Conboy JC. High-Throughput Screening of Drug-Lipid Membrane Interactions via Counter-Propagating Second Harmonic Generation Imaging. Analytical Chemistry 2011;83:5979-88.

Sly KL, Nguyen TT, Conboy JC. Lens-less surface second harmonic imaging. Opt Express. 2012;20:21953-67.

Sly KL, Mok S-W, Conboy JC. Second Harmonic Correlation Spectroscopy: A Method for Determining Surface Binding Kinetics and Thermodynamics. Analytical Chemistry. 2013;85:8429-35.

Sly KL, Conboy John C. Determination of Multivalent Protein-Ligand Binding Kinetics and Energetics Using Second Harmonic Correlation Spectroscopy Analytical Chemistry 2014;86:11045-11054.

Kazane SA, Sok D, Cho EH, Uson ML, Kuhn P, Schultz PG, et al. Site-specific DNA-antibody conjugates for specific and sensitive immuno-PCR. Proceedings of the National Academy of Sciences of the United States of America. 2012;109:3731-6.

Law W-C, Yong K-T, Baev A, Prasad PN. Sensitivity Improved Surface Plasmon Resonance Biosensor for Cancer Biomarker Detection Based on Plasmonic Enhancement. ACS Nano. 2011;5:4858-64.

Krishnan S, Mani V, Wasalathanthri D, Kumar CV, Rusling JF. Attomolar Detection of a Cancer Biomarker Protein in Serum by Surface Plasmon Resonance Using Superparamagnetic Particle Labels. Angew Chem, Int Ed. 2011;50:1175-8, S/1-S/4.

Panikkanvalappil SR, Mackey MA, El-Sayed MA. Probing the Unique Dehydration-Induced Structural Modifications in Cancer Cell DNA Using Surface Enhanced Raman Spectroscopy. Journal of the American Chemical Society. 2013;135:4815-21.

Wu G, Datar RH, Hansn KM, Thundat T, Cote RJ, Majumdar A. Bioassay of prostate-specific antigen (PSA) using microcantilevers. Nat Biotechnol. 2001;19:856-60.

Labib M, Khan N, Ghobadloo SM, Cheng J, Pezacki JP, Berezovski MV. Three-Mode Electrochemical Sensing of Ultralow MicroRNA Levels. Journal of the American Chemical Society. 2013;135:3027-38.

Chikkaveeraiah BV, Bhirde AA, Morgan NY, Eden HS, Chen X. Electrochemical Immunosensors for Detection of Cancer Protein Biomarkers. ACS Nano. 2012;6:6546-61.

Rana S, Singla AK, Bajaj A, Elci SG, Miranda OR, Mout R, et al. Array-Based Sensing of Metastatic Cells and Tissues Using Nanoparticle-Fluorescent Protein Conjugates. ACS Nano. 2012;6:8233-40.

Rusling JF, Kumar CV, Gutkind JS, Patel V. Measurement of biomarker proteins for point-of-care early detection and monitoring of cancer. Analyst (Cambridge, U K). 2010;135:2496-511.

Li J, Li S, Yang CF. Electrochemical biosensors for cancer biomarker detection. Electroanalysis. 2012;24:2213-29.

Swierczewska M, Liu G, Lee S, Chen X. High-sensitivity nanosensors for biomarker detection. Chem Soc Rev. 2012;41:2641-55.

Alberti D, Erve Mvt, Stefania R, Ruggiero MR, Tapparo M, Geninatti Crich S, et al. A Quantitative Relaxometric Version of the ELISA Test for the Measurement of Cell Surface Biomarkers. Angew Chem, Int Ed. 2014;53:3488-91.

Stokes G, Conboy John C. Measuring Selective Estrogen Receptor Modulator (SERM)—Membrane Interactions with Second Harmonic Generation. JACS. 2014;136(4):1409-17.

Chang-Yen DA, Myszka D, Gale Bka. A novel PDMS microfluidic spotter for fabrication of protein chips and microarrays. Proc SPIE. 2005;5718:111.

Wennmalm S, Edman L, Rigler R. Conformational fluctuations in single DNA molecules. Proceedings of the National Academy of Sciences of the United States of America. 1997;94(20):10641-6.

Hall WP, Ngatia SN, Van Duyne RP. LSPR Biosensor Signal Enhancement Using Nanoparticle-Antibody Conjugates. Journal of Physical Chemistry C. 2011;115(5):1410-4.

Zhavnerko GK, Yi SJ, Chung SH, Yuk JS, Ha KS. Oriented immobilization of C-reactive protein on solid surface for biosensor applications. NATO Science Series, II: Mathematics, Physics and Chemistry. 2004;152(Frontiers of Multifunctional Integrated Nanosystems):95-108.

Cooper MA. Optical biosensors in drug discovery. Nature Reviews Drug Discovery. 2002;1(7):515-28.

Barrett-Connor E, Mosca L, Collins P, Geiger MJ, Grady D, Kornitzer M, et al. Effects of Raloxifene on Cardiovascular Events and Breast Cancer in Postmenopausal Women. New England Journal of Medicine. 2006;355(2):125-37.

Morello KC, Wurz GT, DeGregorio MW. Pharmacokinetics of Selective Estrogen Receptor Modulators. Clinical Pharmacokinetics. 2003;42(4):361-72.

Koppel DE, Axelrod D, Schlessinger J, Elson EL, Webb WW. Dynamics of fluorescence marker concentration as a probe of mobility. Biophysical Journal. 1976;16(11):1315-29.

Thompson NL, Navaratnarajah P, Wang X. Measuring Surface Binding Thermodynamics and Kinetics by Using Total Internal Reflection with Fluorescence Correlation Spectroscopy: Practical Considerations. Journal of Physical Chemistry B. 2011;115(1):120-31.

Starr TE, Thompson NL. Total internal reflection with fluorescence correlation spectroscopy: combined surface reaction and solution diffusion. Biophysical Journal. 2001;80(3):1575-84.

Thompson NL, Burghardt TP, Axelrod D. Measuring surface dynamics of biomolecules by total internal reflection fluorescence with photobleaching recovery or correlation spectroscopy. Biophysical Journal. 1981;33(3):435-54.

Maiti S, Haupts U, Webb WW. Fluorescence correlation spectroscopy: diagnostics for sparse molecules. Proceedings of the National Academy of Sciences of the United States of America. 1997;94(22):11753-7.

Golovan LA, Melnikov VA, Bestem'Yanov KP, Zabotnov SV, Gordienko VM, Timoshenko VY, et al. Disorder-correlated enhancement of second-harmonic generation in strongly photonic porous gallium phosphide. Applied Physics B: Lasers and Optics. 2005;81(2-3):353-6.

Shi J, Yang T, Kataoka S, Zhang Y, Diaz AJ, Cremer Ps. GM1 Clustering Inhibits Cholera Toxin Binding in Supported Phospholipid Membranes. Journal of the American Chemical Society. 2007;129(18):5954-61.

(56) References Cited

OTHER PUBLICATIONS

Jung H, Yang T, Lasagna MD, Shi J, Reinhart GD, Cremer PS. Impact of hapten presentation on antibody binding at lipid membrane interfaces. Biophysical Journal. 2008;94(8):3094-103.
Hirano S-I, Yogo T, Kikuta K-I, Noda K-I, Ichida M, Nakamura A. Synthesis of KTiOPO4 (KTP) thin films using metallo-organics. Journal of the American Ceramic Society. 1995;78(11):2956-60.
Polanski M, Anderson Nl. A List of Candidate Cancer Biomarkers for Targeted Proteomics. Biomarker Insights. 2006;1:1-48.
Mor G, Visintin I, Lai Y, Zhao H, Schwartz P, Rutherford T, et al. Serum protein markers for early detection of ovarian cancer. Proceedings of the National Academy of Sciences of the United States of America. 2005;102:7677-82.
Xiao T, Ying W, Li L, Hu Z, Ma Y, Jiao L, et al. An approach to studying lung cancer-related proteins in human blood. Mol Cell Proteomics. 2005;4:1480-6.
Jemal A, Siegel R, Ward E, Hao Y, Xu J, Murray T, et al. Cancer Statistics, 2008. CA: A Cancer Journal for Clinicians. 2008;58(2):71-96.
Rhea JM, Molinaro RJ. Cancer biomarkers: surviving the journey from bench to bedside. MLO: medical laboratory observer. 2011;43(3):10-2, 6, 8; quiz 20, 2.
Polanski M, Anderson N. A list of candidate cancer biomarkers for targeted proteomics. Biomarker Insights. 2007;1:1-48.
Mattson G, Conklin E, Desai S, Nielander G, Savage MD, Morgensen S. A practical approach to crosslinking. Molecular Biology Reports. 1993;17(3):167-83.
Yoshitake S, Imagawa M, Ishikawa E, Niitsu Y, Urushizaki I, Nishiura M, et al. Mild and efficient conjugation of rabbit Fab' and horseradish peroxidase using a maleimide compound and its use for enzyme immunoassay. Journal of Biochemistry. 1982;92(5):1413-24.
Loo LN, Capobianco JA, Wu W, Gao X, Shih WY, Shih W-H, et al. Highly sensitive detection of HER2 extracellular domain in the serum of breast cancer patients by piezoelectric microcantilevers. Analytical Chemistry (Washington, DC, United States). 2011;83:3392-7.
Conboy JC, Kriech MA. Measuring melittin binding to planar supported lipid bilayer by chiral second harmonic generation. Anal Chim Acta. 2003;496:143-53.
Evans-Nguyen KM, Fuierer RR, Fitchett BD, Tolles LR, Conboy JC, Schoenfisch MH. Changes in Adsorbed Fibrinogen upon Conversion to Fibrin. Langmuir. 2006;22:5115-21.
Kriech MA, Conboy JC. Using the intrinsic chirality of a molecule as a label-free probe to detect molecular adsorption to a surface by second harmonic generation. Appl Spectrosc. 2005;59:746-53.
Nguyen TT, Sly KL, Conboy JC. Comparison of the Energetics of Avidin, Streptavidin, NeutrAvidin, and Anti-Biotin Antibody Binding to Biotinylated Lipid Bilayer Examined by Second-Harmonic Generation. Analytical Chemistry 2012;84:201-8.
Garcia-Schwarz G, Santiago JG. Rapid High-Specificity microRNA Detection Using a Two-stage Isotachophoresis Assay. Angew Chem, Int Ed. 2013; 52:11534-7.
Samanta A, Maiti KK, Soh K-S, Liao X, Vendrell M, Dinish US, et al. Ultrasensitive Near-Infrared Raman Reporters for SERS-Based In Vivo Cancer Detection. Angew Chern, Int Ed. 2011;50:6089-92, S/1-S/23.
Li M, Cushing SK, Zhang J, Suri S, Evans R, Petros WP, et al. Three-Dimensional Hierarchical Plasmonic Nano-Architecture Enhanced Surface-Enhanced Raman Scattering Immunosensor for Cancer Biomarker Detection in Blood Plasma. ACS Nano. 2013;7:4967-76.
Song Y, Wei W, Qu X. Colorimetric Biosensing Using Smart Materials. Adv Mater (Weinheim, Ger). 2011; 23:4215-36.
Mizusawa K, Takaoka Y, Hamachi I. Specific Cell Surface Protein Imaging by Extended Self-Assembling Fluorescent Turn-on Nanoprobes. Journal of the American Chemical Society. 2012;134:13386-95.
Wu L, Qu X. Cancer biomarker detection: recent achievements and challenges. Chem Soc Rev. 2015;44:2963-97.
Luo X, Davis JJ. Electrical biosensors and the label free detection of protein disease biomarkers. Chem Soc Rev. 2013;42:5944-62.
de la Rica R, Stevens MM. Plasmonic ELISA for the ultrasensitive detection of disease biomarkers with the naked eye. Nat Nanotechnol. 2012; 7:821-4.
Reen DJ. Enzyme-linked immunosorbent assay (ELISA). Methods Mol Biol (Totowa, N J). 1994;32:461-6.
Jackson TM, Ekins RP. Theoretical limitations on immunoassay sensitivity: Current practice and potential advantages of fluorescent Eu3+ chelates as non-radioisotopic tracers. Journal of Immunological Methods. 1986;87(1):13-20.
Kriech MA, Conboy JC. Label-free chiral detection of melittin binding to a membrane. Journal of the American Chemical Society. 2003;125:1148-9.
Zhang F, Gates RJ, Smentkowski VS, Natarajan S, Gale BK, Watt RK, et al. Direct Adsorption and Detection of Proteins, Including Ferritin, onto Microlens Array Patterned Bioarrays. Journal of the American Chemical Society. 2007; 129(30):9252-3.
Natarajan S, Hatch A, Myszka DG, Gale BK. Optimal Conditions for Protein Array Deposition Using Continuous Flow. Anal Chem. 2008;80:8561-7.
Magde D, Elson EL, Webb WW. Fluorescence correlation spectroscopy. II. Experimental realization. Biopolymers. 1974;13(1):29-61.
Eddings MAea. Improved continuous-flow print head for microarray deposition. Anal Biochem. 2008;382:55-9.
Grunwell JR, Glass JL, Lacoste TD, Deniz AA, Chemla DS, Schultz PG. Monitoring the Conformational Fluctuations of DNA Hairpins Using Single-Pair Fluorescence Resonance Energy Transfer. Journal of the American Chemical Society. 2001;123(18):4295-303.
Ladd J, Boozer C, Yu Q, Chen S, Homola J, Jiang S. DNA-Directed Protein Immobilization on Mixed Self-Assembled Monolayers via a Streptavidin Bridge. Langmuir. 2004;20(19):8090-5.
Esseghaier C, Helali S, Ben Fredj H, Tlili A, Abdelghani A. Polypyrrole-neutravidin layer for impedimetric biosensor. Sensors and Actuators, B: Chemical. 2008;B131(2):584-9.
Sun H, Choy TS, Zhu DR, Yam WC, Fung YS. Nano-silver-modified PQC/DNA biosensor for detecting E. coli in environmental water. Biosensors & Bioelectronics. 2009;24(5):1405-10.
Bashir R, Gomez R, Sarikaya A, Ladisch MR, Sturgis J, Robinson JP. Adsorption of avidin on microfabricated surfaces for protein biochip applications. Biotechnology and Bioengineering. 2001;73(4):324-8.
Lazcka O, Del Campo FJ, Munoz FX. Pathogen detection: A perspective of traditional methods and biosensors. Biosensors & Bioelectronics. 2007;22(7):1205-17.
Barton AC, Davis F, Higson SPJ. Labeless Immunosensor Assay for the Stroke Marker Protein Neuron Specific Enolase Based upon an Alternating Current Impedance Protocol. Analytical Chemistry (Washington, DC, United States). 2008;80(24):9411-6.
Teeter JS, Meyerhoff RD. Environmental fate and chemistry of raloxifene hydrochloride. Environmental Toxicology and Chemistry. 2002;21(4):729-36.
Dodge JA, Lugar CW, Cho S, Short LL, Sato M, Yang NN, et al. Evaluation of the major metabolites of raloxifene as modulators of tissue selectivity. The Journal of Steroid Biochemistry and Molecular Biology. 1997;61(1-2):97-106.
Dutertre M, Smith CL. Molecular Mechanisms of Selective Estrogen Receptor Modulator (SERM) Action. Journal of Pharmacology and Experimental Therapeutics. 2000;295(2):431-7.
Magde D, Elson E, Webb WW. Thermodynamic fluctations in a reacting system. Measurement by fluorescence correlation spectroscopy. Physical Review Letters. 1972; 29(11):705-8.
Hansen RL, Harris JM. Measuring reversible adsorption kinetics of small molecules at solid/liquid interfaces by total internal reflection fluorescence correlation spectroscopy. Anal Chem. 1998;70(20):4247-56.
Watanabe H, Yamaguchi S, Sen S, Morita A, Tahara T. "Half-hydration" at the air/water interface revealed by heterodyne-detected electronic sum frequency generation spectroscopy, polarization second harmonic generation, and molecular dynamics simulation. J Chem Phys. 2010;132:144701/1-/9.
Frostell-Karlsson A, Remaeus A, Roos H, Andersson K, Borg P, Haemaelaeinen M, et al. Biosensor Analysis of the Interaction

(56) References Cited

OTHER PUBLICATIONS between Immobilized Human Serum Albumin and Drug Compounds for Prediction of Human Serum Albumin Binding Levels. Journal of Medicinal Chemistry. 2000;43(10):1986-92.

Murtaza R, Jackman HL, Alexander B, Lleshi-Tali A, Winnie AP, Igic R. Simultaneous determination of mepivacaine, tetracaine, and p-butylaminobenzoic acid by high-performance liquid chromatography. Journal of Pharmacological and Toxicological Methods. 2001;46(3):131-6.

Haes AJ, Van Duyne RP A nanoscale optical biosensor: Sensitivity and selectivity of an approach based on the localized surface plasmon resonance spectroscopy of triangular silver nanoparticles. Journal of the American Chemical Society. 2002;124(35):10596-604.

Zhao S, Walker DS, Reichert WM. Cooperativity in the binding of avidin to biotin-lipid-doped Langmuir-Blodgett films. Langmuir. 1993;9(11):3166-73.

Vornholt W, Hartmann M, Keusgen M. SPR studies of carbohydrate—lectin interactions as useful tool for screening on lectin sources. Biosensors and Bioelectronics. 2007; 22(12):2983-8.

Li D, Kong L, Zhang L, Yao X. Sol-gel preparation and characterization of transparent $KTiOPO_4/SiO_2$ nanocomposite glass for second harmonic generation. Journal of Non-Crystalline Solids. 2000;271(1,2):45-55.

Cook GB, Neaman IE, Goldblatt JL, Cambetas DR, Hussain M, Luftner D, et al. Clinical utility of serum HER-2/neu testing on the bayer Immuno 1 automated system in breast cancer. Anticancer Research. 2001;21(2B):1465-70.

Gann PH, Hennekens CH, Stampfer MJ. A prospective evaluation of plasma prostate-specific antigen for detection of prostatic cancer. JAMA : the journal of the American Medical Association. 1995;273(4):289-94.

Yamaguchi K, Nagano M, Torada N, Hamasaki N, Kawakita M, Tanaka M. Urine diacetylspermine as a novel tumor marker for pancreatobiliary carcinomas. Rinsho Byori. 2004; 52:336-9.

Ciambellotti E, Coda C, Lanza E. Determination++ of CA 15-3 in the control of primary and metastatic breast carcinoma. Minerva Med. 1993;84(Copyright (C) 2013 U.S. National Library of Medicine.):107-12.

Liu J, Eddings MA, Miles AR, Bukasov R, Gale BK, Shumaker-Parry JS. In situ microarray fabrication and analysis using a microfluidic flow cell array integrated with surface plasmon resonance microscopy. Anal Chem. 2009;81:4296-301.

Natarajan S, Hatch A, Myszka David G, Gale Bruce K. Optimal conditions for protein array deposition using continuous flow. Anal Chem. 2008;80(22):8561-7.

* cited by examiner

| Analyte | SH | | SPR | | Fluorescence | | ELISA | |
|---|---|---|---|---|---|---|---|---|
| | fM | pg/cm² | fM | pg/cm² | fM | pg/cm² | fM | pg/cm² |
| Ibuprofen | 227.3 ± 0.1 | 46.9 ± 4.7 | 415 | 95 | | | | |
| Tetracaine | 441.4 ± 41.2 | 116.7 ± 10.9 | 835 | 1918 | | | 5900000 | 1562000 |
| SBN | 0.040 ± 0.001 | 114 ± 4 | 415 | 95 | | | | |
| Cocaine | 130±70 pM | 370±200n g/cm² | | | | | 2900±10 00pM | 8200±2200n g/cm² |
| Tolnaftate | 4251.0 ± 172 | 1306.8 ± 52.8 | 202507 5 | 623723 | | | | |
| Azithromyci n | 4.8 ± 0.4 | 3.6 ± 0.3 | 533 | 405 | | | | |
| Streptavidin | 84 ± 17 | 4413 ± 883 | 0.06 | 3 | 433 | 22872 | | |
| Cholera Toxin B | 0.7 ± 0.1 | 44.6 ± 6.6 | 7 | 393 | 5 | 285 | 3 | 195 |
| Avidin | 80.1 ± 0.3 | 5280 ± 17 | 0.06 | 4 | 433 | 28578 | | |
| Peanut Agglutinin | 40.3 ± 3.7 | 4433 ± 407 | 50169 | 5511000 | 1562 | 171784 | | |
| Anti-biotin | 17 ± 0.9 | 2384 ± 119 | 50169 | 7023660 | 3 | 429 | 0.005 | 0.5 |

FIG. 2

| Marker | Disease | Cut Off | Sensitivity | Specificity |
|---|---|---|---|---|
| Her-2/neu | stage IV breast cancer | 15 ng/mL | 40% | 98% |
| PSA | prostate cancer | 4.0 ng/mL | 46% | 91% |
| CA19.9 | pancreatic cancer | NA | 75% | 80% |
| CA 15.3 | breast cancer | 40 U/ml | 58.2% | 96.0% |
| leptin, prolactin, osteopontin, and IGF-II | ovarian cancer | NA | 95% | 95% |
| CD98, fascin, sPIgR, and 14-3-3 eta | lung cancer | NA | 96% | 77% |

FIG. 4

Bind antigen/drug to antibody

Langmuir Model:

$$\frac{I}{I_{max}} \propto \left(\frac{K_a[c]}{1+K_a[c]}\right)^2$$

SYSTEMS AND METHODS FOR LABEL-FREE DETECTION OF ANALYTES

CROSS-REFERENCE TO RELATED APPLICATIONS

This application claims benefit of U.S. Provisional Application No. 62/284,412, filed Sep. 29, 2015, which is hereby incorporated herein by reference in its entirety.

STATEMENT REGARDING FEDERALLY SPONSORED RESEARCH

This invention was made with government support under Grant number RO1 GM068120 awarded by the National Institutes of Health and Grant number CHE1110351 awarded by the National Science Foundation. The government has certain rights in the invention.

BACKGROUND

A simple cancer biomarker assay can provide early cancer detection and identification so that individualized treatment strategies can be delivered to patients in a timely manner. Such assays also have the potential to track progression, regression, and recurrence of the disease. When considering the multitude of potential cancer biomarkers, one area which has been largely overlooked is the low-molecular weight (LMW) distribution of peptides and protein fragments which are present in blood, saliva and urine. These LMW species (haptens) are either directly secreted or are produced from the degradation of larger protein products of cancer cells. LMW biomarkers have traditionally been excluded from development due to the difficulty in detecting these species in an easy and reliable manner. The standard approaches used to date employ a competitive immunoassay with the hapten immobilized on a solid-support and binding of the primary antibodies to the surface is in competition with the analyte (e.g. free hapten) in solution. Detection is typically achieved using an enzyme-linked immunosorbant assay (ELISA) platform. Though this approach is the current "gold standard" in clinical assays, competitive assays suffer from a limited dynamic range and poor detection limits. In addition, the development of appropriate secondary antibodies is also required and the method can also suffer from "antibody interference". The detection and quantification of LMW cancer biomarkers in a label-free fashion using a primary antibody capture assay would circumvent the limitations of current competitive immunoassays and would represent a significant advancement in the ability to rapidly screen patients for potential cancers in a cost effective and efficient manner.

BRIEF SUMMARY

Disclosed are methods of detecting an analyte of interest comprising introducing a sample comprising an analyte of interest to an antibody or antibody fragment, incubating the sample and antibody or antibody fragment under conditions sufficient to allow binding of the analyte of interest to the antibody or antibody fragment, and detecting the binding of the analyte of interest to the antibody or antibody fragment using a label-free second harmonic detection system.

Disclosed are methods of screening for analytes that bind an antibody or antibody fragment comprising introducing an analyte to an antibody or antibody fragment, and detecting the presence of the analyte bound to the antibody or antibody fragment using a label-free second harmonic detection system, wherein the presence of the analyte bound to the antibody or antibody fragment indicates the analyte binds the antibody or antibody fragment.

Disclosed are methods of diagnosing cancer in a subject comprising introducing a sample obtained from a subject to an antibody or antibody fragment, detecting the presence of an analyte bound to the antibody or antibody fragment using a label-free second harmonic detection system, diagnosing the subject with cancer when the presence of the analyte bound to the antibody or antibody fragment is detected, and administering a therapeutically effective amount of an anticancer treatment to the diagnosed subject.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2 is a comparison of the LOD for Second Harmonic (SH), Surface Plasmon Resonance (SPR), Fluorescence and Enzyme Linked ImmunoSorbent Assay (ELISA).

FIG. 4 shows a list of candidate cancer biomarkers for targeted proteomics.

FIG. 6A shows the molecular structures of cocaine and methadone (left) and the corresponding extinction coefficients (M−1cm−1) as a function wavelength (nm) (right), and FIG. 6B is a schematic of the immobilization procedure used to link the primary antibodies to the solid support.

FIG. 7A shows the SH binding isotherms of cocaine and methadone to anti-cocaine antibody immobilized on the sensor surface, and FIG. 7B is a schematic representation of the cocaine/anti-cocaine antibody capture event, with the corresponding Langmuir adsorption isotherm model used to fit the data shown in FIG. 7A.

FIG. 9A is the autocorrelation of cocaine binding to anti-cocaine antibody measured using SHCS, and FIG. 9B is the autocorrelation of methadone binding to anti-methadone antibody measured using SHCS. The corresponding association ($k_{on}$) and dissociation ($k_{off}$) rates and the measured affinity constants ($K_a$) obtained from the SHCS data are also displayed.

DETAILED DESCRIPTION

Figure 1A:
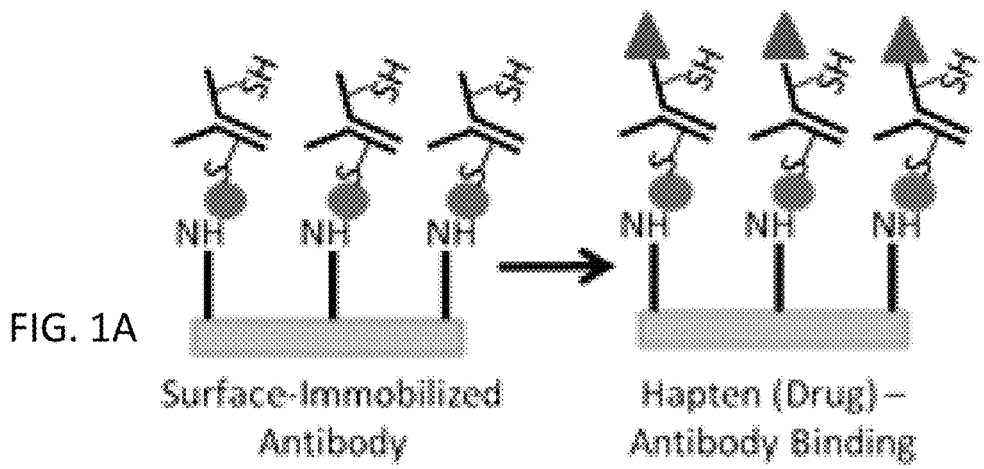
FIGS. 1A-1D show the detection of cocaine binding via the label-free SH immunoassay and a control of methadone binding to an anti-cocaine antibody as a control. Second harmonic correlation spectroscopy (SHCS) analysis of the same binding experiment. Both methods obtain the same binding data with the SHCS method also providing the association and dissociation rates in about 1/10th the time.
Figure 1B:
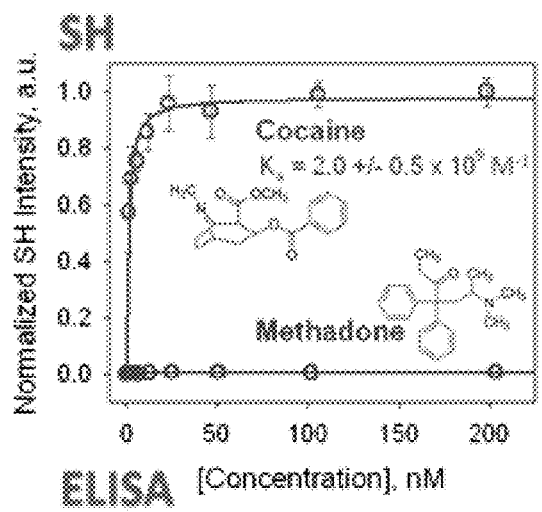
Figure 1C:
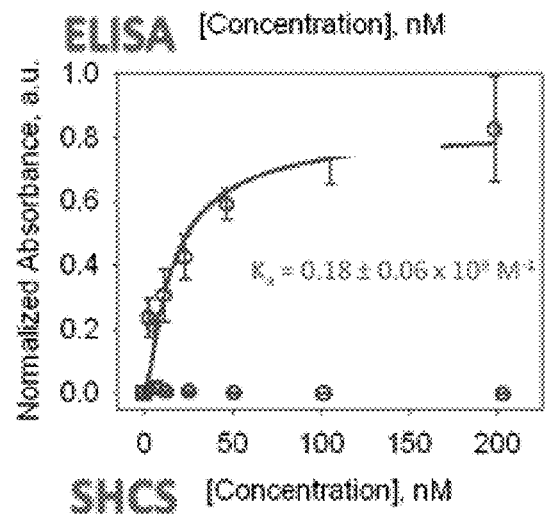
Figure 1D:
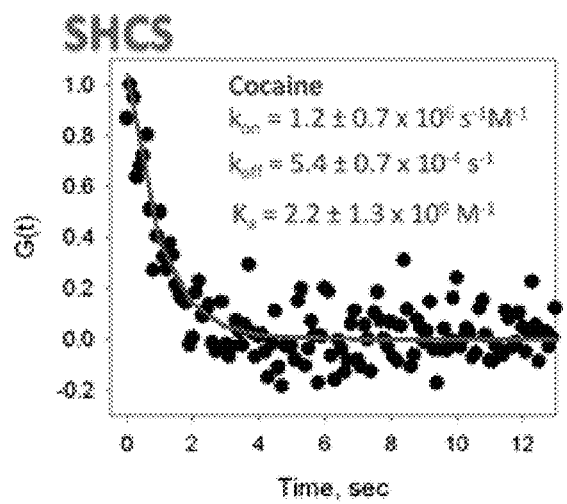

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an analyte of interest is disclosed and discussed, each and every combination and permutation of an analyte of interest and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-R, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary, it is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a support layer" includes a plurality of such support layers, reference to "the support layer" is a reference to one or more support layers and equivalents thereof known to those skilled in the art, and so forth.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition, such as but not limited to cancer. In some instances, a therapeutically effective amount is an amount of a therapeutic that provides a therapeutic benefit to an individual.

As used herein, the term "subject" or "patient" refers to any organism to which a composition of this invention may be administered, e.g., for experimental, diagnostic, and/or therapeutic purposes. Typical subjects include animals (e.g., mammals such as non-human primates and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range—from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

As used herein, the term "label-free" refers to a system or method that is capable of providing information regarding molecular interactions without the need for an exogenous label.

As used herein, the term "analyte of interest" refers to a substance whose chemical constituent is of interest in an analytical procedure such as a procedure to identify or measure the substance. An "analyte of interest" can be any substance, including, but not limited to, a nucleic acid, peptide, protein, antibody, or a small molecule.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Detection Systems

Disclosed are systems for detecting an analyte of interest using the methods described herein. Optionally, the system can be a second harmonic detection system, such as, for example, a label-free second harmonic detection system. Exemplary configurations of a label-free second harmonic detection system are disclosed herein. However, it is contemplated that the disclosed methods can be performed using any configuration of an optical imaging system that is capable of measuring and detecting second harmonic signals as disclosed herein.

In exemplary aspects, and with reference to FIGS. 12A-12C, the label-free second harmonic detection system can comprise a light source, such as a laser, that generates incident light at a first frequency. Optionally, the laser can be a Nd:YAG laser as is known in the art. In exemplary aspects, it is contemplated that the laser can be a Nd:YAG pumped optical parametric oscillator (OPO) laser as is known in the art. In these aspects, it is further contemplated that the laser can be tunable within a wavelength range of about 400 nm to about 2,000 nm. In some aspects, it is contemplated that the incident light produced by the laser can have a wavelength ranging from about 200 nm to about 1,000 nm. Thus, in exemplary aspects, the wavelength of the incident light can range from about 200 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, or from about 900 nm to about 1,000 nm. Optionally, in exemplary aspects, the wavelength can be about 532 nm. It is further contemplated that the optical parametric oscillator can be pumped with a selected pulse width ranging from about 10 fs to about 10 ns and at a selected repetition rate ranging from about 1 Hz to about 1 MHz. It is contemplated that these parameters can be selectively adjusted depending on system characteristics and process conditions. In use, it is contemplated that the laser can be pulsed in a manner such that the pulse width and pulse energy associated with the resulting beam provide a power density of least 100 kW/cm$^2$.

Optionally, as shown in FIGS. 12A-12B, the second harmonic detection system can comprise a telescope assembly that receives a beam from the laser (optionally, after the beam has passed through at least one polarizer) and selectively adjusts (optionally, reduces) a diameter of the beam to a selected size (e.g., about 2 mm$^2$).

In further aspects, the second harmonic detection system can further comprise a substrate assembly for supporting a sample. For example, in some aspects, the substrate assembly can have a prism layer and a support layer that supports the sample between the support layer and the prism layer. In these aspects, it is contemplated that the portion of the prism layer in contact with the sample can be planar or substantially planar. In exemplary aspects, the prism layer can comprise an optical material that is transparent at both the excitation and second-harmonic wavelengths. Optionally, the prism layer can comprise silicon oxide or fused silica; however, it is contemplated that other types of prisms can be used. In exemplary aspects, it is contemplated that the sample can be deposited on or otherwise secured to the prism layer or the support layer using conventional methods. For example, in these aspects, an aqueous solution containing the analyte of interest can be placed in direct contact with the prism layer through the use of a flow-cell or similar device as is known in the art. In use, the substrate assembly receives incident light at a first frequency from the laser, and the incident light is reflected at the interface between the support layer and the sample. Optionally, the laser can be configured to direct light to the prism layer—and the prism layer can be oriented—such that the incident light is perpendicular or substantially perpendicular to an outer surface of the prism layer where the incident light enters the prism. In exemplary aspects, the incident light can be delivered to the prism layer at a selected angle of incidence ranging from about 5 to about 85 degrees. Optionally, in various aspects and as shown in FIG. 12C, it is contemplated that the support layer of the substrate assembly can comprise a flow cell for performing spectroscopic measurements. In these aspects, the flow cell can be provided within a TEFLON block or other suitable chemically-resistant material to which the prism layer is mounted. Optionally, the flow cell can be provided with at least one port (optionally, two ports on opposing sides of the block) to permit exchange of the cell volume. Optionally, in further aspects, the flow cell can be provided with additional ports for monitoring temperature and pH as needed. In exemplary aspects, the flow cell can be provided with at least one window that allow for detection of light at the second harmonic wavelength through the window. Optionally, such a window can be positioned on an opposed side of the flow cell from the sample. Thus, in addition to detecting light at the second harmonic wavelength that is reflected from the top surface of the sample, it is contemplated that the disclosed system can be configured to detect light at the second harmonic wavelength that is transmitted through the window. Optionally, the system can be configured to only detect light at the second harmonic wavelength that is transmitted through the window. Thus, it is contemplated that any desired orientation of the substrate assembly can be used.

Optionally, in additional aspects, the second harmonic detection system can comprise a mirror, such as a high-power dielectric mirror, that reflects light back toward the sample (and the surface of the prism layer supporting the sample) after incident light is reflected. As shown in FIG. 12C, the light reflected by the mirror can be provided at the same wavelength as the incident light. In exemplary aspects, the angle of incidence of the light reflected by the mirror (toward the sample) can be equal to the angle of incidence of the light provided by the first light source.

Alternatively, in other optional aspects, the system does not include a mirror. In these aspects, it is contemplated that the system can comprise a second light source that delivers light at a frequency equal to the first frequency (delivered by the first light source). In exemplary aspects, the angle of incidence of the light provided by the second light source can be equal to the angle of incidence of the light provided by the first light source.

The second harmonic detection system can further comprise a detection assembly that receives reflected light from the substrate assembly after the incident light and the light reflected by the mirror (or the light provided by a second light source) contact the sample and cooperate to generate a second harmonic signal. As disclosed herein, the detection assembly can detect a second harmonic signal corresponding to reflected light having a second frequency equal to twice the first frequency. In exemplary aspects, the detection assembly can comprise a monochromator or other filtering element that is configured to remove scattered fundamental light. In additional aspects, as shown in FIG. 12B, it is contemplated that the detection assembly can comprise a photomultiplier tube (PMT) that detects a second harmonic signal as further disclosed herein. Additionally or alternatively, it is contemplated that the detection assembly can comprise a charge-coupled device (CCD) detector that is configured to detect a second harmonic signal as further disclosed herein. In use, it is contemplated that the photomultiplier tube and CCD can be configured to detect light at the second harmonic wavelength.

In further exemplary aspects, the second harmonic detection system can comprise a processing assembly that receives the second harmonic signal and determines a quantity of an analyte of interest as further disclosed herein. In these aspects, the processing assembly can be communicatively coupled (by wired or wireless connection) to the detection assembly. Optionally, in exemplary aspects, the processing assembly can comprise a gated integrator and boxcar averager as are known in the art. Additionally, or alternatively, the processing assembly can comprise a computing device, such as a computer, a tablet, a smartphone, a server, a network, a Cloud-based device, and the like, that is communicatively coupled to the detection assembly. It is contemplated that the computing device can have processing circuitry that is coupled to a memory for accessing software or data to assist with analysis of an analyte as disclosed herein.

Figure 3A:
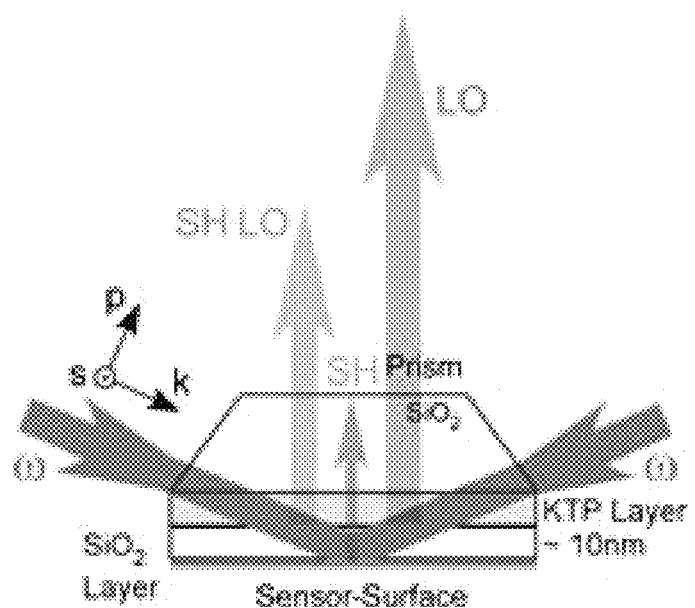
FIG. 3A is a schematic of a SH heterodyning method disclosed herein.

In further optional aspects, and as shown in FIG. 3A, the detection assembly can comprise a sensor having a first surface that receives reflected, second-harmonic light from the substrate assembly. It is contemplated that the first surface of the sensor can comprise any suitable material that is optically transparent at both the second harmonic and excitation wavelengths. In these aspects, it is contemplated that the first surface of the sensor can be optically heterodyned to amplify the second harmonic signal. For example, in one exemplary non-limiting configuration, the first surface of the sensor can be covered with a non-linear optically-active surface layer, such as for example and without limitation, potassium titanyl phosphate (KTP). Optionally, the non-linear optically-active surface layer can be directly deposited onto the first surface of the sensor. The non-linear optically-active surface layer can be covered with a silicon oxide sol-gel film to create a self-contained heterodyne optical arrangement. It is contemplated that the surface layers can be applied using a conventional sol-gel process as is known in the art. Alternatively, it is contemplated that the non-linear optically-active surface layer can comprise a thin crystalline material or other non-linear optically-active material that is attached to the first surface using an adhesive or bonding agent. In use, it is contemplated that the heterodyned sensor can be configured to enhance the second harmonic signal as further disclosed herein.

C. Methods of Detecting

Disclosed are methods of detecting an analyte of interest comprising introducing a sample comprising an analyte of interest to an antibody or antibody fragment, incubating the sample and antibody or antibody fragment under conditions sufficient to allow binding of the analyte of interest to the antibody or antibody fragment, and detecting the binding of the analyte of interest to the antibody or antibody fragment using a label-free second harmonic detection system.

In some instances, an analyte of interest can be a protein, nucleic acid, small molecule, or fragment thereof. In some instances, the fragment thereof of any of the protein, nucleic acid, or small molecule can comprise the binding site for the disclosed antibody or antibody fragment. In some instances, an analyte of interest can be a biomarker. For example, an analyte of interest can be a cancer biomarker. For example, a cancer biomarker can be, but is not limited to, BRCA1/BRCA2, CEA, EGFR, HER-2, PSA, S100, BCR-ABL, p53, or p14ARF. In some instances, an analyte of interest is a low molecular weight protein or fragment thereof. For example, low molecular weight proteins can be, but are not limited to, cytokines, chemokines, peptide hormones, or proteolytic fragments of larger proteins.

In some instances, a sample can be a biological sample. For example, a biological sample can be, but is not limited to, blood, serum, urine, milk, cell lysate, tissue lysate, plasma, tears, sweat, or ocular fluid. In some instances, a sample can be derived from a food source, wherein the sample can be used for detecting contaminants.

In some instances, an antibody or antibody fragment is known to bind the analyte of interest. In some instances, an antibody or antibody fragment can be immobilized on a support. For example, the support can be a solid support. In some instances, a solid support can be a solid-state substrate or support with which antibodies or antibody fragments can be immobilized directly or indirectly. In some instances the antibody fragment at least comprises the Fab portion of a full length antibody. In some instances the antibody fragment at least comprises the variable region of a full length antibody.

Solid supports can include any solid material to which antibodies or antibody fragments can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polygly colic acid, polylactic acid, polyorthoesters, polypropylfumerate, collagen, glycosaminoglycans, and polyamino acids. Solid supports can have any useful form including thin film, membrane, bottles, dishes, fibers, woven fibers, shaped polymers, particles, beads, microparticles, or a combination. Solid supports can be porous or non-porous. A form for a solid-state substrate is a microliter dish, such as a standard 96-well type.

Methods for immobilizing antibodies (and other proteins) to solid supports are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy]succinimide ester (GMBS). These and other attachment agents, as well as methods for their use in attachment, are described in Protein immobilization: fundamentals and applications, Richard F. Taylor, ed. (M. Dekker, New York, 1991), Johnstone and Thorpe, Immunochemistry In Practice (Blackwell Scientific Publications, Oxford, England, 1987) pages 209-216 and 241-242, and Immobilized Affinity Ligands; Craig T. Hermanson et al., eds. (Academic Press, New York, 1992) which are incorporated by reference in their entirety for methods of attaching antibodies to a solid support. Antibodies can be attached to a support by chemically cross-linking a free amino group on the antibody to reactive side groups present within the solid support. For example, antibodies may be chemically cross-linked to a support that contains free amino, carboxyl, or sulfur groups using glutaraldehyde, carbodiimides, or GMBS, respectively, as cross-linker agents. In this method, aqueous solutions containing free antibodies are incubated with the solid support in the presence of glutaraldehyde or carbodiimide.

A method for attaching antibodies or other proteins to a solid support is to functionalize the support with an amino- or thiol-silane, and then to activate the functionalized support with a homobifunctional cross-linker agent such as (Bis-sulfo-succinimidyl suberate (BS3) or a heterobifunctional cross-linker agent such as GMBS. For cross-linking with GMBS, glass supports are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated support, which are then blocked with solutions containing agents such as 2% bovine serum albumin, and air-dried. Other standard immobilization chemistries are known by those of skill in the art.

Disclosed are methods of detecting an analyte of interest comprising introducing a sample comprising an analyte of interest to an antibody or antibody fragment, incubating the sample and antibody or antibody fragment under conditions sufficient to allow binding of the analyte of interest to the antibody or antibody fragment, and detecting the binding of the analyte of interest to the antibody or antibody fragment using a label-free second harmonic detection system, wherein the concentration of the analyte in the sample is sub-femtomolar. In some instances, the concentration of the analyte in the sample can be sub-micromolar, sub-nanomolar, sub-picomolar, or sub-femtomolar. In some instances, the concentration of the analyte of interest in the sample can be micromolar to sub-femtomolar.

Disclosed are methods of detecting an analyte of interest comprising introducing a sample comprising an analyte of interest to an antibody or antibody fragment, incubating the sample and antibody or antibody fragment under conditions sufficient to allow binding of the analyte of interest to the antibody or antibody fragment, and detecting the binding of the analyte of interest to the antibody or antibody fragment using a label-free second harmonic detection system, further comprising a step of washing away any unbound analyte prior to detecting the binding of the analyte of interest.

In some aspects, the disclosed composition and methods can be used in drug screening of a subject. For example, antibodies or antibody fragments capable of binding to a drug or drug metabolite can be used in the methods disclosed herein. As shown herein, methods of detecting cocaine and methadone in a sample can be performed using the methods disclosed herein.

In some aspects, the disclosed composition and methods can be used to detect a contaminant in a food. For example, a sample from a food source can be screened using the methods disclosed herein to determine the presence of a particular analyte of interest (e.g. a contaminant).

1. Introducing a Sample Comprising an Analyte of Interest to an Antibody or Antibody Fragment;

In some instances, introducing a sample comprising an analyte of interest to an antibody or antibody fragment comprises adding the sample comprising an analyte of interest to the antibody or antibody fragment. In some instances, the antibody or antibody fragment can be in a solution, immobilized to a support or a combination thereof.

In some instances, introducing a sample comprising an analyte of interest to an antibody or antibody fragment comprises adding the antibody or antibody fragment to a sample comprising an analyte of interest. In some instances, the antibody or antibody fragment bound to the analyte of interest can be subsequently immobilized to a support prior to detection.

2. Incubating the Sample and Antibody or Antibody Fragment Under Conditions Sufficient to Allow Binding of the Analyte of Interest to the Antibody or Antibody Fragment; and In some instances, incubating the sample and antibody or antibody fragment under conditions sufficient to allow binding of the analyte of interest to the antibody or antibody fragment comprises providing incubation conditions such as appropriate temperature, pH and salt concentration to allow binding of the analyte of interest to the antibody or antibody fragment. In some instances, incubating the sample and antibody or antibody fragment under conditions sufficient to allow binding of the analyte of interest to the antibody or antibody fragment comprises providing appropriate concentrations of the antibody or antibody fragment to bind the analyte of interest.

3. Detecting the Binding of the Analyte of Interest to the Antibody or Antibody Fragment Using a Label-Free Second Harmonic Detection System.

In some instances, detecting the binding of the analyte of interest to the antibody or antibody fragment using a label-free second harmonic detection system makes use of non-linear optical methods such as second-harmonic imaging (SHI) and second-harmonic correlation spectroscopy (SHCS) to produce a detection scheme for a universal, label-free immunoassay as further disclosed herein.

In exemplary aspects, detecting the binding of the analyte of interest to the antibody or antibody fragment using the label-free second harmonic detection system can comprise using second harmonic imaging (SHI) to detect the binding of the analyte of interest. In additional aspects, detecting the binding of the analyte of interest to the antibody or antibody fragment using the label-free second harmonic detection system can further comprise determining binding properties of the analyte of interest using second-harmonic correlation spectroscopy. Optionally, detecting the binding of the analyte of interest to the antibody or antibody fragment using the label-free second harmonic detection system can comprise using second-harmonic correlation spectroscopy to determine binding affinity data (e.g., $K_a$, $K_d$, and the like) for the analyte of interest based upon a single measured concentration of the analyte of interest. The second-harmonic signal can be recorded as a function of time at a single analyte concentration. The resulting signal can then be correlated automatically to retrieve the dynamics of the binding process. The resulting correlation is then numerically fit to the follow equation:

$$G(\tau) = \frac{k_{off}}{k_{on}[A]} \times \exp[-(k_{on}[A] + k_{off})\tau]$$

Using sing a nonlinear least squares regression algorithm, the parameters, $k_{on}$ and $k_{off}$ can be obtained. Additionally, detecting the binding of the analyte of interest to the antibody or antibody fragment using the label-free second harmonic detection system can further comprise using second-harmonic imaging to quantify the analyte of interest. The second-harmonic imaging can be accomplished by direct collection of a wide field image using a CCD device using a large illumination area which covers the entirely or a fraction of the sensor area. Alternatively, the second-harmonic imaging can be accomplished by raster scanning of the incident excitation source over the surface in such a way as to construct and image from individual collection points based on the location of the excitation source on the surface using a PMT or other suitable photon detector system.

Optionally, in additional aspects and as previously described, the label-free second harmonic detection system can comprise: a laser that generates incident light at a first frequency; a substrate assembly having a prism layer and a support layer that supports the sample and antibody or antibody fragment between the support layer and the prism layer, wherein the substrate receives incident light at the first frequency from the laser; a detection assembly that receives reflected light from the substrate assembly, wherein the detection assembly detects a second harmonic signal corresponding to reflected light having a second frequency equal to twice the first frequency; and a processing assembly that receives the second harmonic signal and determines a quantity of the analyte of interest. In further optional aspects, and as previously described, it is contemplated that the detection assembly can comprise a sensor having a first surface that receives reflected light from the substrate assembly. In these aspects, it is contemplated that the first surface of the sensor can be optically heterodyned to amplify the second harmonic signal. For example, in one exemplary non-limiting configuration, the first surface of the sensor can be covered with a non-linear optically-active surface layer, and the non-linear optically-active surface layer can be covered with a silicon oxide sol-gel film to create a self-contained heterodyne optical arrangement that enhances the second harmonic signal.

D. Methods of Screening

Disclosed are methods of screening for analytes that bind an antibody or antibody fragment comprising introducing an analyte to an antibody or antibody fragment, and detecting the presence of the analyte bound to the antibody or antibody fragment using a label-free second harmonic detection system, wherein the presence of the analyte bound to the antibody or antibody fragment indicates the analyte binds the antibody or antibody fragment.

In some instances, an antibody or antibody fragment is known to bind the analyte of interest. In some instances, an antibody or antibody fragment can be immobilized on a support. For example, the support can be a solid support. In some instances, a solid support can be a solid-state substrate or support with which antibodies or antibody fragments can be immobilized directly or indirectly. In some instances the antibody fragment at least comprises the Fab portion of a full length antibody. In some instances the antibody fragment at least comprises the variable region of a full length antibody.

In some instances, an analyte of interest can be a protein, nucleic acid, small molecule, or fragment thereof. In some instances, the fragment thereof of any of the protein, nucleic acid, or small molecule can comprise the binding site for the disclosed antibody or antibody fragment. In some instances, an analyte of interest can be a biomarker. For example, an analyte of interest can be a cancer biomarker. For example, a cancer biomarker can be, but is not limited to, BRCA1/BRCA2, CEA, EGFR, HER-2, PSA, S100, BCR-ABL, p53, or p14ARF. In some instances, an analyte of interest is a low molecular weight protein or fragment thereof. For example, low molecular weight proteins can be, but are not limited to, cytokines, chemokines, peptide hormones, or proteolytic fragments of larger proteins.

In exemplary aspects, detecting the presence of the analyte bound to the antibody or antibody fragment using the label-free second harmonic detection system can comprise using second harmonic imaging (SHI) to detect the binding of the analyte to the antibody or antibody fragment as further disclosed herein. In further exemplary aspects, it is contemplated that detecting the presence of the analyte bound to the antibody or antibody fragment using the label-free second harmonic detection system can comprise determining binding properties of the analyte of interest using second-harmonic correlation spectroscopy as further disclosed herein.

E. Methods of Diagnosing

Disclosed are methods of diagnosing cancer in a subject comprising introducing a sample obtained from a subject to an antibody or antibody fragment, detecting the presence of an analyte bound to the antibody or antibody fragment using a label-free second harmonic detection system, diagnosing the subject with cancer when the presence of the analyte bound to the antibody or antibody fragment is detected, and administering a therapeutically effective amount of an anti-cancer treatment to the diagnosed subject. In some instances, the subject is human.

In some instances, a sample can be a biological sample. For example, a biological sample can be, but is not limited to, blood, serum, urine, milk, cell lysate, tissue lysate, plasma, tears, sweat, or ocular fluid.

In some instances, an analyte of interest can be a protein, nucleic acid, small molecule, or fragment thereof. In some instances, the fragment thereof of any of the protein, nucleic acid, or small molecule can comprise the binding site for the disclosed antibody or antibody fragment. In some instances, an analyte of interest can be a biomarker. For example, an analyte of interest can be a cancer biomarker. For example, a cancer biomarker can be, but is not limited to, BRCA1/BRCA2, CEA, EGFR, HER-2, PSA, S100, BCR-ABL, CA-125, p53, or p14ARF. In some instances, an analyte of interest is a low molecular weight protein or fragment thereof. For example, low molecular weight proteins can be, but are not limited to, cytokines, chemokines, peptide hormones, or proteolytic fragments of larger proteins.

In some instances, the anti-cancer treatment can be any known anti-cancer treatment including, but not limited to, chemotherapy, radiation, immunotherapy, cell therapy, or hormone therapy.

In exemplary aspects, detecting the presence of the analyte bound to the antibody or antibody fragment using the label-free second harmonic detection system can comprise using second harmonic imaging (SHI) to detect the binding of the analyte to the antibody or antibody fragment. In further exemplary aspects, detecting the presence of the analyte bound to the antibody or antibody fragment using the label-free second harmonic detection system can comprise determining binding properties of the analyte of interest using second-harmonic correlation spectroscopy.

F. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting an analyte of interest, the kit comprising an antibody or antibody fragment and at least one component of a label-free second harmonic detection system. The kits also can contain a solid support.

The disclosed kits can also include instructions for how to use the label-free second harmonic detection system.

EXAMPLES

Cancer biomarkers have the potential of providing a reliable detection scheme for early cancer detection, identification and progression, allowing patients to receive the most effective and appropriate therapies. The presence of cancer in a patient generates a unique signature in the blood, through the presence of LMW proteins and peptides originating from cancer cells in the body. A multitude of specific biomarkers and their effective concentrations in the blood need to be evaluated to provide an accurate assessment of the state, type and progression of cancer in a patient. The goal of this proposal is not to identify such markers, but to implement a feasible multiplexed array based detection assay for quantification and identification of such biomarkers in a clinical setting.

There have been a number of analytical approaches taken to detect and quantify cancer biomarkers in blood and other biological samples, including the polymerase chain reaction (PCR), capillary electrophoresis, surface plasmon resonance (SPR), surface enhanced Raman spectroscopy (SERS), microcantilevers, colorimetric assays, electrochemical assays, and a variety of fluorescence methods. These approaches and others have been summarized in a number of recent reviews. Competitive enzyme-linked immunosorbent assays (ELISAs), have also been employed, which is not surprising due to their extensively used in clinical diagnostics for decades. They are also considered the gold standard for the detection of proteins in physiological samples by many.

Traditionally, detection of LMW substances in blood, salvia or urine have been carried out using competitive heterogeneous ELISA based immunoassays employing immobilized antibodies or small-molecule conjugates on a solid support. Competitive immunoassays are simple, rapid and cost-effective methods for detecting a wide range of LMW analytes in variety of biological matrixes. However, the number of commercially available immunoassay kits for haptens is relatively limited. The surprising absence of antibody based assays for haptens in the marketplace is due largely to the poor performance (reproducibility) and high limits of detection (LOD) typically associated with the current tests. An alternative would be to use a noncompetitive assay. A study reviewing the fundamental problems associated with competitive immunoassays showed that they are inferior to noncompetitive immunoassays in terms of sensitivity, precision, kinetics and dynamic range of the analyte. However, a practical noncompetitive hapten immunoassay format has not been forthcoming, due to the difficulty of detecting the hapten upon capture. Clearly, the development of a noncompetitive cancer biomarker assay would overcome the limitations of existing competitive ELISA tests, but the detection problem is the largest hurdle to overcome in developing a functional noncompetitive or primary antibody assay.

1. Developing a Label-Free Noncompetitive Cancer Biomarker Immunoassay

The prevalence of cancer and the need for early detection makes the development of accurate, rapid, cost effective assays of paramount importance. The goal here is to apply SHCS and SHI to develop a label-free noncompetitive immunoassay for cancer biomarkers. Initial studies allow for method validation of the approach and characterization in biological matrices (bovine plasma or urine) can prove the viability of the assay in a clinically relevant platform. These studies present a comprehensive examination of the efficacy of SHCS and Second Harmonic Imaging (SHI) for the label-free detection of cancer biomarkers in a primary antibody immunoassay format. These studies can advance the ability to detect a host of biologically relevant molecules and biomarkers associated with cancer, significantly improving upon existing clinical assays.

It is estimated that greater than 1 million people annually are diagnosed with cancer of some form. The high prevalence of cancer and the need for early detection makes the development of accurate, rapid, cost effective and widely available assays of paramount importance. The ability to detect low concentrations of cancer biomarkers (fM and lower) is also highly desirable. From an analytical perspective, lower LODs lead to earlier detection and more favorable outcomes for patients.

A recent examination of bottlenecks in the development of clinical assays for cancer detection based on biomarkers found that the reason behind so few biomarkers reaching the clinic can largely be explained by the inability of current technologies to consistently and quantitatively verify the presence of the candidates (biomarkers) in patient samples. Clearly an accurate, highly sensitive, label-free noncompetitive immunoassay would be of clinical relevance for the screening of potential cancer biomarkers.

There are approximately 1200 proteins which have been identified as potential biomarkers for various forms of cancer. However, only 9 have been FDA approved for cancer screening. In order to validate SHCS and SHI for biomarker detection, 6 FDA approved biomarkers (FIG. 4) will be screened in a primary antibody array using SHI and SHCS. These candidates were chosen principally because existing working assays exist with established LODs. The proteins and primary antibodies needed to create the arrays are also commercially available.

Figure 10A:
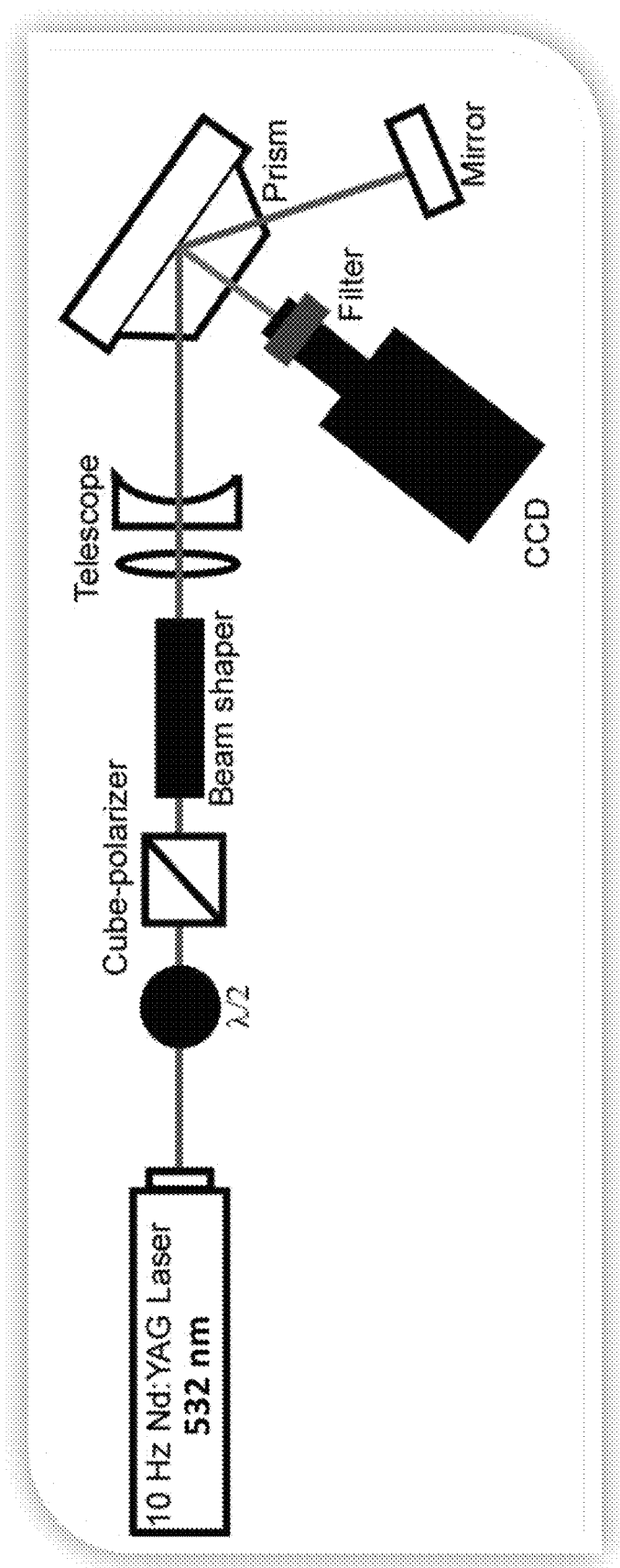
FIG. 10A depicts an exemplary second harmonic detection system including a charge-coupled device detector.
Figure 10:
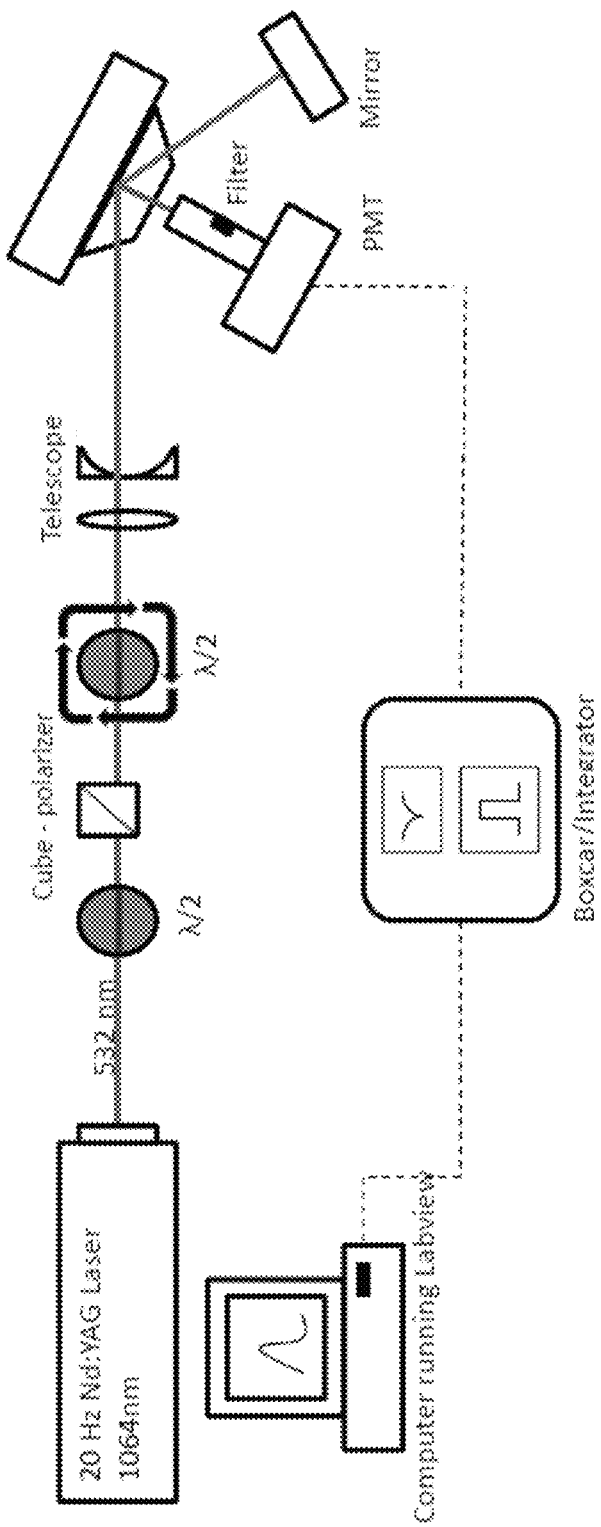
FIG. 10B depicts another exemplary second harmonic detection system including a photomultiplier tube and a processing assembly as disclosed herein.
FIG. 10C schematically depicts a counter-propagating second harmonic generation configuration as further disclosed herein.
Figure 10:
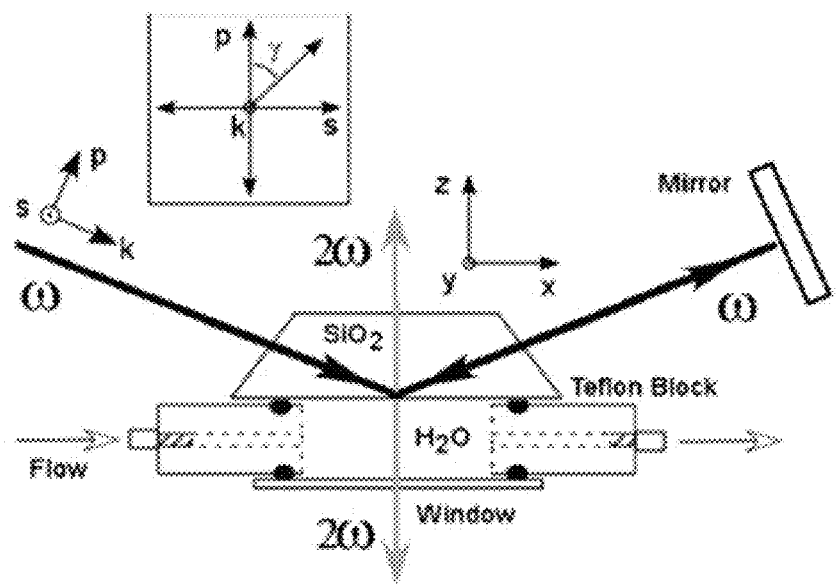

The approach described herein uses the nonlinear optical process of second harmonic (SH) generation for the label-free detection of cancer biomarkers in an immunoassay format SH is a coherent second-order nonlinear optical technique which is inherently surface-specific and possesses the spectroscopic characteristics of UV-Vis absorbance spectroscopy. The principles of SH have been discussed in a number of excellent reviews. SH involves the frequency doubling of an incident optical field at frequency $\omega$ yielding photons at twice the frequency ($2\omega$) of the incident source (FIG. 10C). The frequency doubling can be modeled using the following equation: $2\omega=\omega_{vis}+\omega_{vis}$. The measured SH intensity is proportional to the square of the surface density of molecules coupled with the surface-specificity of the technique, makes it ideally suited for detection in a heterogeneous assay. The surface selectivity eliminates the need for a "washing" step, allowing a true equilibrium measurement to be made, which is crucial when sub-micromolar (µM) concentrations of analytes are measured and overcomes the largest source of error in current competitive ELISA based immunoassays. If the fundamental ($\omega$) or SH ($2\omega$) frequencies are resonant with electronic transitions of the small-molecule, peptide or protein of interest, an increase in the SH signal is observed. The SH signal can be modeled according to the following equation:

$$\chi_R^{(2)} = \sum_i \frac{NA_i}{\omega_i - \omega_{laser} - i\Gamma_i},$$

where $\omega_j$=resonant transition in UV or Vis.

As almost all small-molecules of biological importance (peptides, proteins or metabolites) contain double bonds or conjugated ring systems with electronic transitions in the UV and deep UV, a considerable SH enhancement is achieved when using a visible pump. The versatility of SH for the label-free detection of various small-molecule drugs, peptides and proteins to model lipid membranes was previously established. SH techniques are also exquisitely sensitive to molecular symmetry; as such, a random orientation of molecules produces no measurable SH due to the symmetry constraints of the up-conversion process. However, when a molecule is specifically bound to a receptor, such as an antibody, the net alignment of the molecules allows for detection (FIG. 1), thus eliminating the need for sophisticated blocking buffers as required in most ELISA-based assays. The capacities of SH have also been extended by developing a new imaging modality. Coupling SHI with a microarray fabrication method using a continuous flow micro-spotter allows for the development of a high-throughput label-free cancer biomarker immunoassay as disclosed herein.

i. Continuous Flow Microspotter for Array Formation

The use of arrays for chemical/biological analysis is well proven, and provides a high-throughput or multiplex advantage. A Continuous Flow Microspotter (CFM) is ideally suited for the creation of biological and molecular arrays. Two unique applications of the CFM are 1) the creation of multicomponent lipid bilayer arrays (MLBAs) and 2) the demonstration of protein capture. The CFM can be used to create discrete lipid bilayers containing a variety of ligands for the selective binding of protein receptors. MLBAs containing lipids functionalized with the GMI ganglioside, DNP and biotin were screened with fluorescently labeled cholera toxin B (CTB), anti-dinitrophenyl (DNP) antibody and NeutrAvidin, in a protein-capture array. The arrays show little to no cross-reactivity and excellent spot-to-spot reproducibility.

ii. Protein and Small-Molecule Detection Using SH

Most conventional microarray-based strategies for detecting proteins, peptides and some small-molecules are based on fluorescence. SH and SHI have been developed to quantify such interaction in a label-free manner. The predominant chromophore in proteins and peptides is the amide backbone. Ignoring contributions from aromatic side chains, this group constitutes the major source of the SH response due to the relatively large nonlinear polarizability of the π electrons. Below are several examples of successes in implementing SH for the detection of proteins and peptides, the detection of small-molecule drugs, and the development of SHI coupled with CFM created arrays for the high-throughput screening of drug-membrane interactions.

a. SH Detection of Proteins and Peptides

Biotin-bound protein complexes have been used in a wide variety of bioanalytical applications, including monitoring conformational changes, biochip sensor fabrication, immunoassays, and targeted drug delivery and screening. A comparison of the binding properties of avidin, streptavidin, neutrAvidin™ and anti-biotin antibody to a biotinylated lipid bilayer was studied using SH, providing a direct comparison of the binding properties of these biotin-protein complexes in a label-free manner and providing an unbiased comparison of the binding affinities.

b. Quantifying Drug-Membrane Interactions

SH was also used to measure the association of several selective estrogen receptor modulator (SERM) drugs to lipid bilayers, to understand how the interaction between the SERMs cell membrane modulates the drugs bioavailability. Tamoxifen and raloxifene are the most widely prescribed SERMs to treat breast cancer and prevent osteoporosis. The binding of raloxifene, tamoxifen and three tamoxifen metabolites to several artificial cell membranes were detected and the differences in membrane interactions for these SERMs and their metabolites were quantified for the first time, and these findings were correlated with their clinical potency.

c. SH Imaging of Small-Molecule Adsorption to Membranes

SH is a powerful tool for investigating small-molecule and protein interactions with membranes in a label-free manner. However, a high-throughput analog would be even more advantageous, akin to fluorescence imaging. Towards that end, SHI was implemented to measure the interactions between the local anesthetic tetracaine and a mid-component lipid bilayer array (MLBA) in a label-free manner allowing the effects of lipid phase and CHO content on tetracaine binding to be examined simultaneously. SHI shows that tetracaine has a higher binding affinity to l.c. phase lipids than to solid-gel phase lipids. The maximum surface excess of tetracaine increases with the degree of unsaturation of the phospholipids and decreases with cholesterol in the lipid bilayers. This study demonstrates that SHI possesses the required sensitivity to directly quantify biomarkers in a high-throughput manner.

iii. Second-Harmonic Correlation Spectroscopy

Determining binding kinetics and subsequent binding affinities in bioassays is technically challenging and time intensive. Typically adsorption and desorption rates are measured in real time, such as in SPR. Another approach which has been used in fluorescence spectroscopy is to measure the fluctuations in a system for a fixed time and through correlation analysis, retrieve the underlying kinetic rates. Although fluorescence correlation spectroscopy (FCS) has been extensively developed and implemented for such surface interactions, the interpretation of the fluorescence autocorrelation data is complicated by fluorescence arising from species in solution, background, fluorescence, and photobleaching.

We have applied the principles of FCS to the label-free and surface specific technique of SH for the first time, overcoming many of the limitations of FCS. Second harmonic correlation spectroscopy (SHCS) eliminates observable fluctuations from molecular diffusion in solution and ameliorates problems associated with the degradation of fluorophores without having to reduce the number of molecules in the observation area, resulting in faster acquisition times and simplified data analysis.

To demonstrate the capabilities of SHCS, the binding kinetics of (S)-(+)-1,1'-bi-2-napthol (SBN) associating with a DOPC lipid bilayer were examined. The results obtained from SHCS were compared to a classical adsorption isotherm experiment to verify the accuracy of the kinetic and thermodynamic values retrieved from the SHCS analysis. Using SHCS, both the adsorption and desorption rates were simultaneously determined in a much shorter time compared to a conventional isotherm study. Additionally, SHCS was used to deconvolute the complex binding properties of multivalent protein-ligand interactions (peanut agglutinin (PnA) and cholera toxin subunit b (CTb) binding to a GM1 which was inaccessible using conventional binding isotherms, SHCS provides amore efficient and comprehensive method for studying molecular interactions at a surface without the need for an exogenous label, providing a new and powerful method for investigating cancer biomarker detection using antibodies, as discussed below.

iv. A Proven Small-Molecule Noncompetitive Label-Free Immunoassay

Figure 5A:
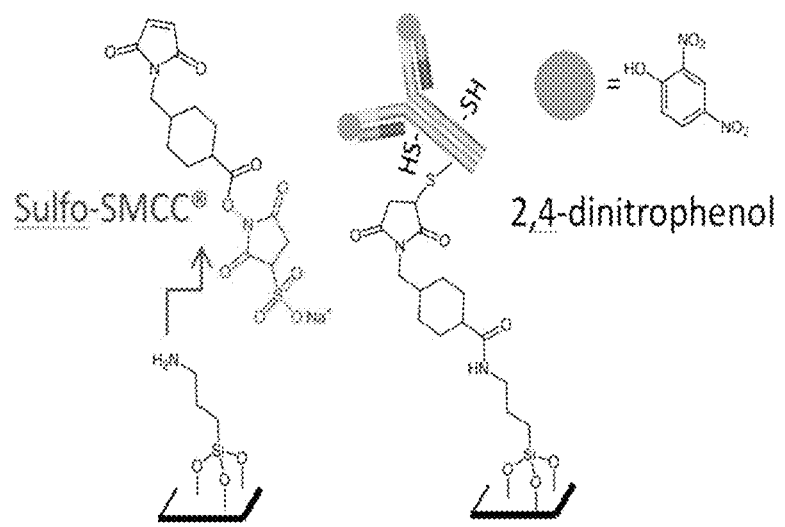
FIG. 5A shows a schematic illustration of an exemplary IgG immobilization procedure.
Figure 5B:
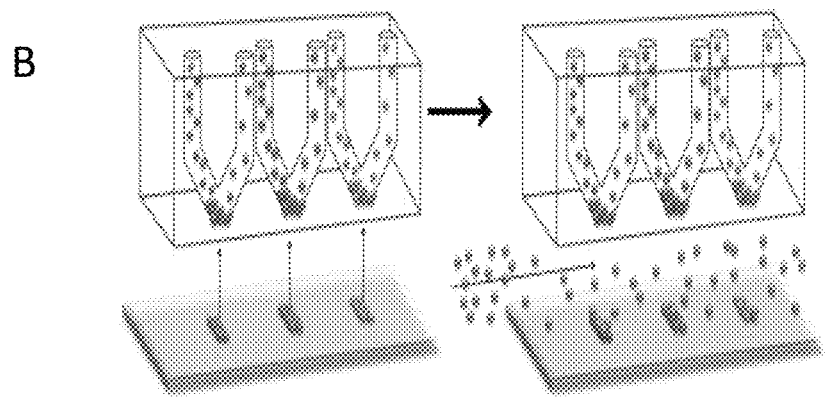
FIG. 5B shows the creation of exemplary antibody arrays using a Continuous Flow Microspotter (CFM) as disclosed herein.
Figure 6A:
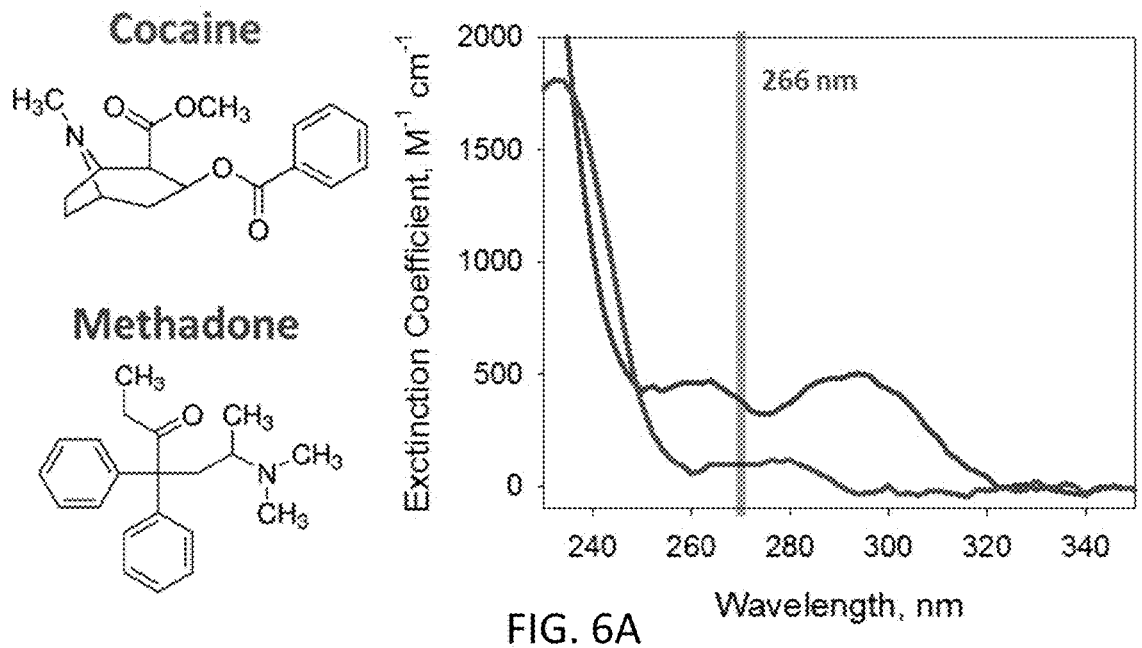
FIGS. 6A-6B show the detection of Cocaine and Methadone in a primary antibody assay.
Figure 6B:
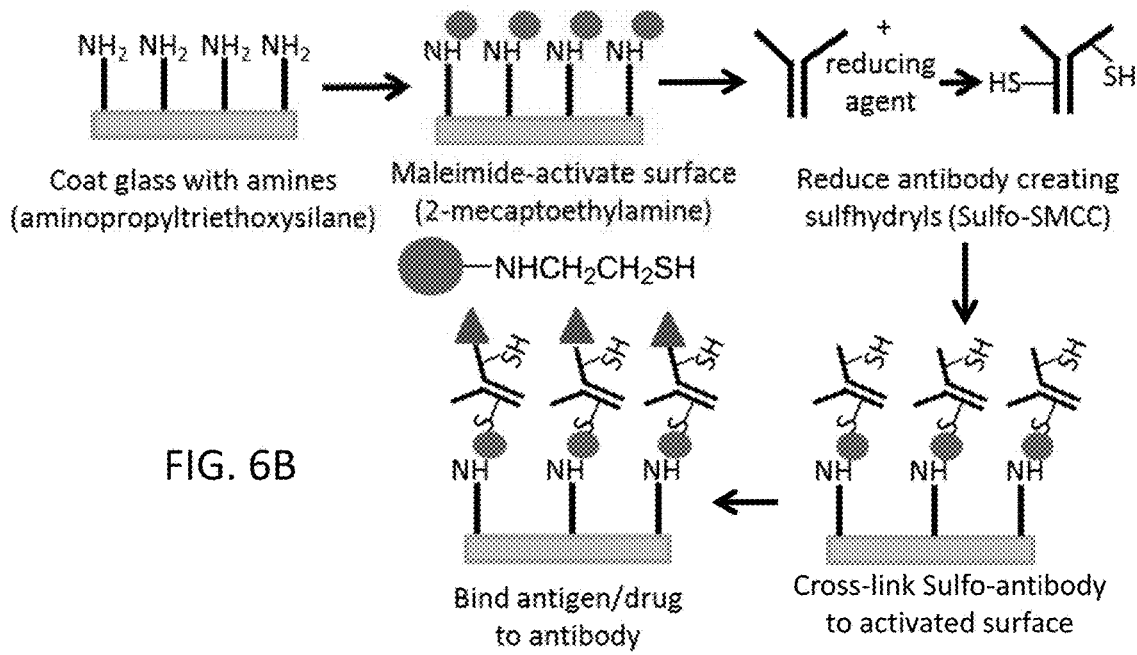
Figure 7A:
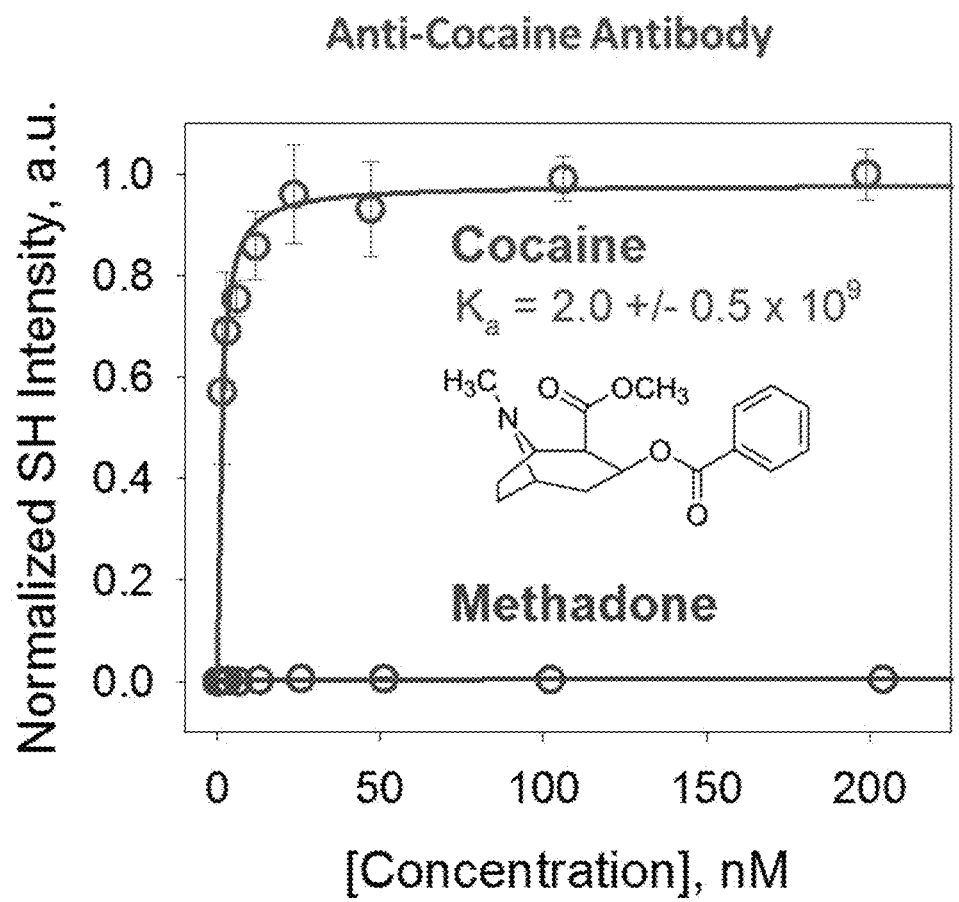
FIGS. 7A-7B show the detection of Cocaine and Methadone in a primary antibody assay.
Figure 7B:
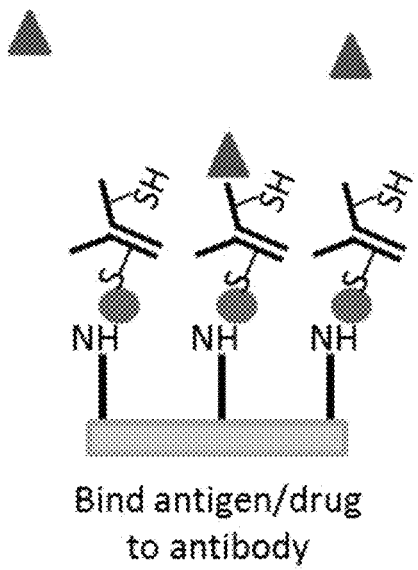
Figure 8:
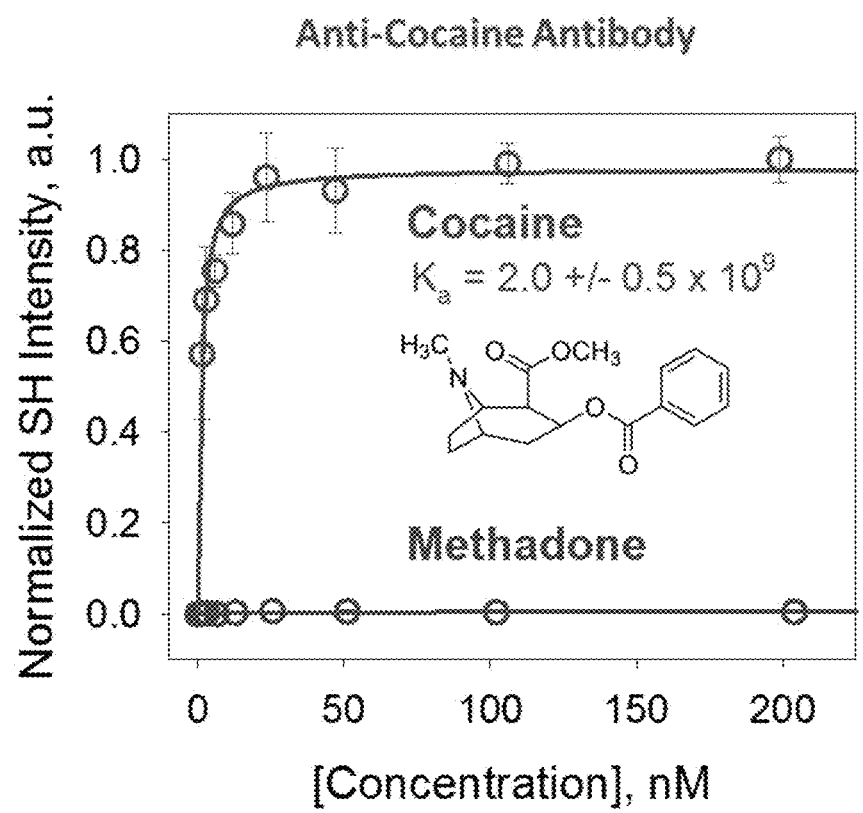
FIG. 8 shows the SH binding isotherms of cocaine and methadone to anti-methadone antibody immobilized on the sensor surface.
Figure 9A:
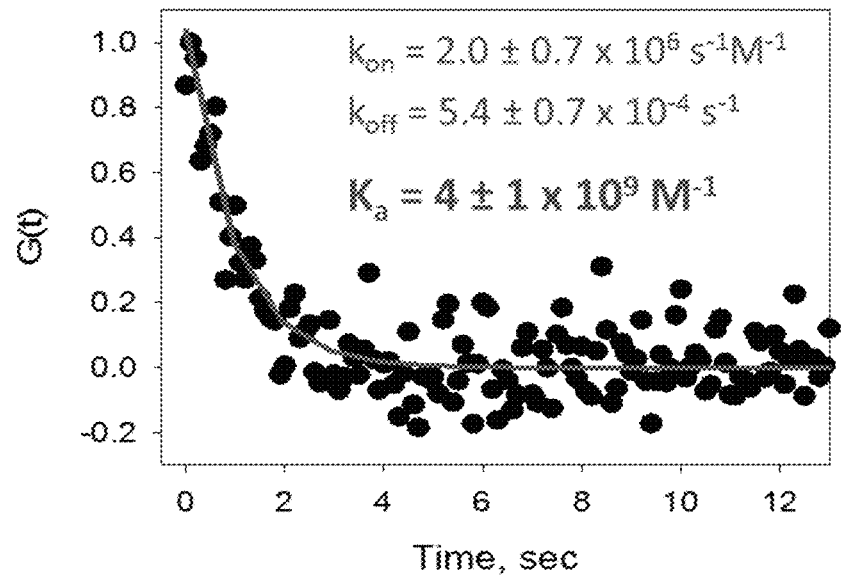
FIGS. 9A-9B show the second harmonic correlation spectroscopy (SHCS) of Cocaine and Methadone.
Figure 9B:
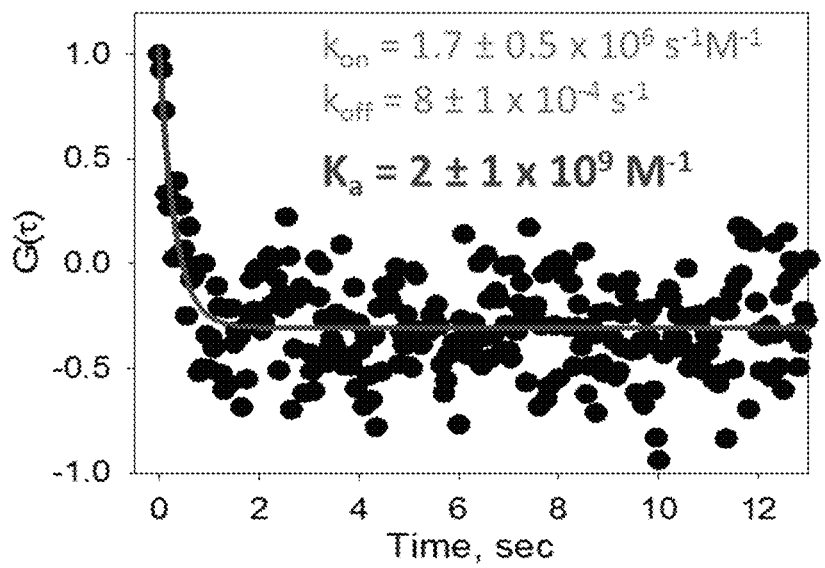

The use of antibodies for the direct detection of LMW small-molecules was not possible using a primary antibody immunoassay format; that is until now. SH and SHCS can detect cocaine (303.4 MW) in a noncompetitive label-free immunoassay with high sensitivity and selectivity (FIG. 1). The LOD is dependent upon the sensitivity (proportional to $K_a$) and noise ($\sigma$). Based on the data in FIG. 1, SH has a 20× lower LOD (0.13±0.07 nM) compared to a standard competitive ELISA (2.9±1 nM). SHCS also provides a rapid assessment of the kinetics of adsorption/desorption and thermodynamic affinity comparable to the isotherm data in a fraction of the time (FIG. 1). The example shown in FIG. 1 for small-molecule capture in a noncompetitive label-free assay using SH illustrates the potential this method has for cancer biomarker detection. Impressive as SH is for the label-free detection of LWM compounds in a noncompetitive immunoassay, improvement of the sensitivity and reducing error in the measurement are crucial for a cancer biomarker assay in order to improve the LOD further. The goal of this research is to reduce the LOD to the fM range for cancer biomarkers detection. The proposed research describes a strategy to achieve this objective by implementing a SH enhancement scheme as disclosed herein.

v. Formation of Antibody Arrays Using the CFM:

Following an established protocol published by Pierce Biotechnology (Tech Tip #5, Thermo Scientific, piercenet.com/fil es/TR0005-Attach-Ab-glass.pdf, FIG. 5), IgG proteins against the various compounds listed in FIG. 4, will be arrayed onto fused silica supports. A silica surface functionalized with 3-aminopropyltrimethoxy silane is reacted with a heterobifunctional cross linker (4-(N-maleimidomethyl)cyclohexane-1-carboxylic acid 3-sulfo-N-hydroxysuccinimide ester sodium salt, i.e. Sulfo-SMCC). The sulfhydryl groups (—SH) on the antibody are made available for covalent coupling to the maleimide-activated surface by reacting native disulfide bonds of the antibody with 2-mercaptoethylamine. The sulthydryl-containing antibodies can be cross-linked to the maleimide-activated silica surface using the CFM.

vi. Screening Cancer Biomarkers:

The representative cancer biomarkers can be reconstituted in PBS, at pH 7.4 and incubated with a primary antibody array for detection. SHCS can be used to calibrate the capture antibody arrays by determining the binding association constant for each of the primary antibody-target biomarker pairs. Using this calibration data, the LOD for the various biomarkers can be determined. The measurement step can be performed using SHI. Cross-reactivity can be examined using antibody arrays for the various markers screened in unison. These measurements can be used to ascertain the specificity of the various capture antibodies for the specific cancer biomarker target.

vii. Screening Libraries in Biologically Relevant Media:

As with the small-molecule immunoassays described in above, the calibration and measurement of biomarker association to the primary antibody arrays can be reproduced in bovine plasma and synthetic urine.

viii. Validation of SHCS and SHI:

The effectiveness of these methods for the screening of the selected cancer biomarkers can be accomplished in two ways: 1) The SHC and SHI approach can be compared to the results obtained using commercially available assays. The LODs, sensitivity and selectively can be measured and compared with the established assays. 2) The ESHC and ESHI results can also be correlated with fluorescence measurements made on the same systems. For the protein biomarker studies, fluorescein (Fl)- or rhodamine (Rh)-labeled analogs of the proteins can be used. Labeling can be accomplished with amine reactive conjugates (lissamine rhodamine B and fluorescein succinimidyl esters, available from invitrogen). Fluorescence microscopy can be used to collect the binding data. The kinetic and steady-state adsorption data obtained by fluorescence can be correlated with that obtained from the SH experiments as a means of validating the SHCS and SHI methods. A statistical assessment of the binding affinities between formats can also be performed as a means of validating the SH detection schemes.

2. Enhancing the Capabilities of Second Harmonic for Cancer Biomarker Detection

One goal of the proposed studies is to enhance and implement the complimentary techniques of SHCS and SHI for the development of a universal, label-free immunoassay for a range of potential LMW cancer biomarkers. SHCS can be implemented for rapid single point calibration to derive the Kd (or Ka) in a fraction of the time required by a conventional thermodynamic equilibrium binding isotherm. This can be coupled with the high-throughput capabilities of SHI for screening and quantifying small-molecules by utilizing antibody capture arrays. Together these methods represent a unique analytical approach which does not compromise sensitivity and speed yet provides a novel label-free immunoassay format. Alone, the techniques are already proven effective label-free methods for detecting proteins and small-molecules, but in order to tackle the changes of detecting cancer biomarkers at the low-levels found in biological samples, the sensitivity of these methods needs to be improved. To achieve this, enhancing these already capable techniques using a novel optical heterodyning method, providing greater sensitivity and improved limit of detection (LOD) can be performed.

The detection limit achievable with the current SH methods is compared with competing technologies SPR, fluorescence, and ELISA (FIG. 2). The data highlights the impressive sensitivity of SH and the clear advantage it has in the label-free detection of both small-molecules and proteins. The studies from which the data in FIG. 2 were obtained are summarized above. As seen in FIG. 2, SH surpasses the detection limits of current state-of-the-art analytical approaches. In most cases, SH has a LOD that is several orders of magnitude better than existing techniques. Although impressive, the LODs still needs to be improved in order to provide a platform capable of detecting the sub-femtomolar (fM) concentrations or lower of cancer biomarkers.

The limited conversion efficiency of nonlinear optical phenomena such as SH underscores the importance of signal enhancement strategies. Enhancement strategies also have the potential to move SH from the laboratory to the clinic by utilizing compact low-cost (~$5K), laser sources. One method which has been used to increase the "signal" in has been optical heterodyning where an external field is "added" to the intrinsically weak SH signal providing significant amplification. The intensity at $2\omega$ ($I_{2\omega}$) for a heterodyned system is given by the following: $[I_{2\omega} \approx (E_{LO})^2 + 2E_{LO}E_{SH}\exp(-i\phi) + E_{SH}^2]$ where $E_{LO}$ is the electric field produced by the local oscillator (LO), $E_{SH}$ is the electric field of the SH generated from the molecules adsorbed at the surface and $\phi$ is the phase difference between LO and SH. $E_{SH} = N < \beta_{ijk} > E(\omega)^2$, with N being the surface density of analyte, $\beta_{ijk}$ is the hyperpolarizability, and $E(\omega)$ is the electric field amplitude of the fundamental field ($\omega$). As $E_{LO}$ is large, the last term in the equation can be negated. The intensity at $2\omega$ is dominated by the LO and the product of the LO and SH fields. As the LO is constant it can be subtracted from the measured intensity, giving an amplified SH response linearly dependent upon the concentration of analyte.

Figure 3B:
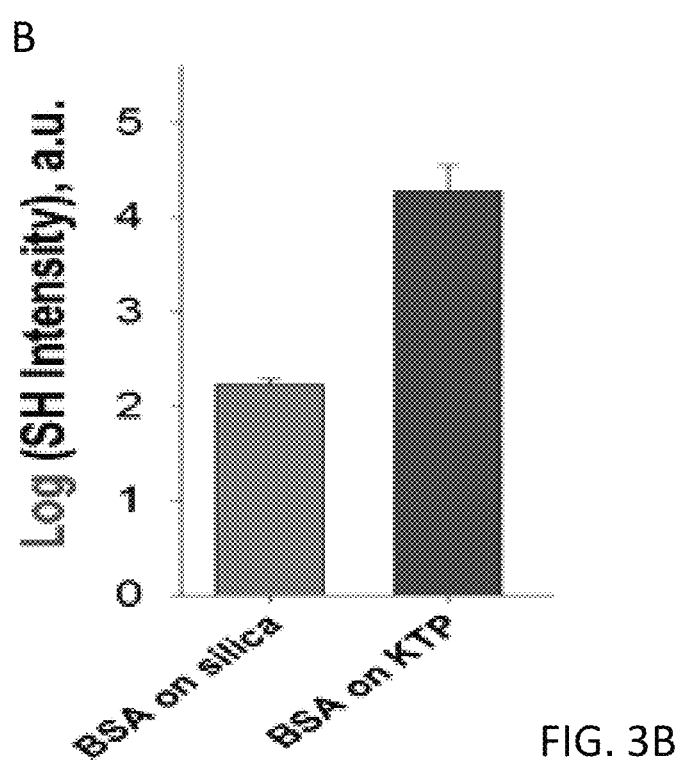
FIG. 3B depicts SH data for an untreated silica surface upon BSA adsorption and the SH heterodyned response from a surface with a KTP layer for amplification in log scale.

Typically optical heterodyning is accomplished with a LO which is generated external to the system. This approach is cumbersome and requires precise optical alignment of the LO with the SH generated at the surface in order to maintain the optimal phase relationship between the LO and SH fields. One exemplary approach, as further disclosed herein, has been to deposit a nonlinear optically-active surface layer, such as potassium titanyl phosphate (KTP), directly onto the sensor surface using the sol-gel process. The 10 nm thick KTP layer is then over-coated with a $SiO_2$ sol-gel film creating a self-contained heterodyne optical arrangement (shown schematically in FIG. 3). The incident field at w generates a fixed-amplitude LO at $2\omega$ in the KTP film which is truly "local" to the surface. This field then combines with the SH providing a >100× enhancement in the SH response. The adsorption of bovine serum albumin (BSA) to the sensor surface was used to measure the achievable gain of these novel KTP-LO films. The goal of Aim #1 is to design and optimize the heterodyne system by varying the nonlinear optical layer thickness and tuning for optimal amplification by varying the thickness of the $SiO_2$ over-layer. The phase difference ($\phi$) between the LO and SH field is given by $\phi = 2\pi n d/\lambda_0$, where n is the refractive index of the $SiO_2$ layer, d is the thickness and $\lambda_0$ is the SH wavelength in a vacuum. It is contemplated that a spectroscopy ellipsometer can aid in the fabrication and characterization of the sensor platform. Based on our preliminary findings, the amplification strategy disclosed herein effectively decreases the LOD of SH by 1-2 orders of magnitude (LOD=$3\sigma$/sensitivity), bringing us into the sub-fM and atoM detection regime. This amplification strategy can be applied to SHCS and SHI, thus enhancing the capabilities of these methods for the detection of cancer biomarkers, as described below.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Smith K A, Gale B K, Conboy J C. Micropatterned Fluid Lipid Bilayer Arrays Created Using a Continuous Flow Microspotter. Analytical Chemistry 2008; 80:7980-7.
2. Conboy J C, Kriech M A. Measuring melittin binding to planar supported lipid bilayer by chiral second harmonic generation. Anal Chim Acta. 2003; 496:143-53.
3. Evans-Nguyen K M, Fuierer R R, Fitchett B D, Tolles L R, Conboy J C, Schoenfisch M H, Changes in Adsorbed Fibrinogen upon Conversion to Fibrin. Langmuir. 2006; 22:5115-21.
4. Kriech M A, Conboy J C. Using the intrinsic chirality of a molecule as a label-free probe to detect molecular adsorption to a surface by second harmonic generation. Appl Spectrosc. 2005; 59:746-53.
5. Nguyen T T, Sly K L, Conboy J C. Comparison of the Energetics of Avidin, Streptavidin, NeutrAvidin, and Anti-Biotin Antibody Binding to Biotinylated Lipid Bilayer Examined by Second-Harmonic Generation. Analytical Chemistry 2012; 84:201-8.
6. Nguyen T T, Rembert K, Conboy J C. Label-Free Detection of Drug-Membrane Association Using Ultraviolet-Visible Sum-Frequency Generation. Journal of the American Chemical Society. 2009; 131:1401-3.
7. Stokes G, Conboy John C. Measuring Selective Estrogen Receptor Modulator (SERM)-Membrane Interactions with Second Harmonic Generation. Journal of the American Chemical Society. 2014; 136:1409-1417.
8. Nguyen T T, Conboy J C. High-Throughput Screening of Drug-Lipid Membrane Interactions via Counter-Propagating Second Harmonic Generation Imaging. Analytical Chemistry 2011; 83:5979-88.
9. Sly K L, Nguyen T T, Conboy J C. Lens-less surface second harmonic imaging. Opt Express. 2012; 20:21953-67.

10. Sly K L, Mok S-W, Conboy J C. Second Harmonic Correlation Spectroscopy: A Method for Determining Surface Binding Kinetics and Thermodynamics. Analytical Chemistry. 2013; 85:8429-35.
11. Sly K L, Conboy John C. Determination of Multivalent Protein-Ligand Binding Kinetics and Energetics Using Second Harmonic Correlation Spectroscopy Analytical Chemistry 2014; 86:11045-11054.
12. Kazane S A, Sok D, Cho E H, Uson M L, Kuhn P, Schultz P G, et al. Site-specific DNA-antibody conjugates for specific and sensitive immuno-PCR. Proceedings of the National Academy of Sciences of the United States of America. 2012; 109:3731-6.
13. Garcia-Schwarz G, Santiago J G. Rapid High-Specificity microRNA Detection Using a Two-stage Isotachophoresis Assay. Angew Chem, Int Ed. 2013; 52:11534-7.
14. Law W-C, Yong K-T, Baev A. Prasad P N. Sensitivity Improved Surface Plasmon Resonance Biosensor for Cancer Biomarker Detection Based on Plasmonic Enhancement. ACS Nano. 2011; 5:4858-64.
15. Krishnan S. Mani V. Wasalathanthri D. Kumar C V, Rusting J F. Attomolar Detection of a Cancer Biomarker Protein in Serum by Surface Plasmon Resonance Using Superparamagnetic Particle Labels. Angew Chem, Int Ed. 2011; 50:1175-8, S/1-S/4.
16. Samanta A, Maiti K K, Soh K-S, Liao X, Vendrell M, Dinish U S, et al, Ultrasensitive Near-Infrared Raman Reporters for SERS-Based In Vivo Cancer Detection. Angew Chem, Int Ed. 2011; 50:6089-92, S/1-S/23.
17. Panikkanvalappil S R, Mackey M A, El-Sayed M A. Probing the Unique Dehydration-Induced Structural Modifications in Cancer Cell DNA Using Surface Enhanced Raman Spectroscopy. Journal of the American Chemical Society. 2013; 135:4815-21.
18. Li M, Cushing S K, Zhang J, Suri S, Evans R, Petros W P, et al. Three-Dimensional Hierarchical Plasmonic Nano-Architecture Enhanced Surface-Enhanced Raman Scattering Immunosensor for Cancer Biomarker Detection in Blood Plasma. ACS Nano. 2013; 7:4967-76.
19. Wu G, Datar R H, Hansn K M, Thundat T, Cote R J, Majumdar A. Bioassay of prostate-specific antigen (PSA) using microcantilevers. Nat Biotechnol. 2001; 19:856-60.
20. Loo L N, Capobianco J A, Wu W, Gao X, Shih W Y, Shih W-H, et al. Highly sensitive detection of HER2 extracellular domain in the serum of breast cancer patients by piezoelectric microcantilevers. Analytical Chemistry (Washington, D.C., United States). 2011; 83:3392-7.
21. Wang J, Wu L, Ren J, Qu X. Visualizing Human Telomerase Activity with Primer-Modified Au Nanoparticles. Small. 2012; 8:259-64.
22. Song Y, Wei W, Qu X. Colorimetric Biosensing Using Smart Materials. Adv Mater (Weinheim, Ger). 2011; 23:4215-36.
23. Labib M, Khan N, Ghobadloo S M, Cheng J, Pezacki J P, Berezovski M V. Three-Mode Electrochemical Sensing of Ultralow MicroRNA Levels. Journal of the American Chemical Society. 2013; 135:3027-38.
24. Chikkaveeraiah B V, Bhirde A A, Morgan N Y, Eden H S, Chen X. Electrochemical Immunosensors for Detection of Cancer Protein Biomarkers. ACS Nano, 2012; 6:6546-61.
25. Rana S, Singla A K, Bajaj A. Elci S G, Miranda O R, Mout R, et al. Array-Based Sensing of Metastatic Cells and Tissues Using Nanoparticle-Fluorescent Protein Conjugates. ACS Nano. 2012; 6:8233-40.
26. Mizusawa K, Takaoka Y, Hamachi I. Specific Cell Surface Protein Imaging by Extended Self-Assembling Fluorescent Turn-on Nanoprobes. Journal of the American Chemical Society. 2012; 134:13386-95.
27. Wu L, Qu X. Cancer biomarker detection: recent achievements and challenges. Chem Soc Rev. 2015; 44:2963-97.
28. Rushing J F, Kumar C V, Gutkind J S, Patel V. Measurement of biomarker proteins for point-of-care early detection and monitoring of cancer. Analyst (Cambridge, U K). 2010; 135:2496-511.
29. Li J, Li S, Yang C F, Electrochemical biosensors for cancer biomarker detection. Electroanalysis. 2012; 24:2213-29.
30. Luo X, Davis J J. Electrical biosensors and the label free detection of protein disease biomarkers. Chem Soc Rev. 2013; 42:5944-62.
31. Swierczewska M, Liu G, Lee S, Chen X. High-sensitivity nanosensors for biomarker detection. Chem Soc Rev. 2012; 41:2641-55.
32. de la Rica R, Stevens M M. Plasmonic ELISA for the ultrasensitive detection of disease biomarkers with the naked eye. Nat Nanotechnol. 2012; 7:821-4.
33. Alberti D, Erve Mvt, Stefania R, Ruggiero M R, Tapparo M, Geninatti Crich S. et al. A Quantitative Relaxometric Version of the ELISA Test for the Measurement of Cell Surface Biomarkers. Angew Chem, Int Ed. 2014; 53:3488-91.
34. Reen D J. Enzyme-linked immunosorbent assay (ELISA). Methods Mol Biol (Totowa, N J). 1994; 32:461-6.
35. Jackson T M, Ekins R P. Theoretical limitations on immunoassay sensitivity: Current practice and potential advantages of fluorescent Eu3+ chelates as non-radioisotopic tracers. Journal of Immunological Methods. 1986; 87(1):13-20.
36. Shen Y R. The Principles of Nonlinear Optics: John Wiley and Sons, Inc; 1984.
37. Stokes G, Conboy John C. Measuring Selective Estrogen Receptor Modulator (SERM)-Membrane Interactions with Second Harmonic Generation. JACS. 2014; 136(4): 1409-17.
38. Kriech M A, Conboy J C. Label-free chiral detection of melittin binding to a membrane. Journal of the American Chemical Society. 2003; 125:1148-9.
39. Dai H-L, Zeng J, editors. Real-time resolved observation of molecular transport through living cell membranes by optical second harmonic generation 2008: American Chemical Society.
40. Muller U R, Nicolau D V, editors. Microarray Technology and its Applications. Berlin Springer-Verlag; 2005.
41. Falciani F, editor. Microarray Technology Through Applications. New York: Taylor and Francis Group; 2007.
42. Zhang F, Gates R J, Smentkowski V S, Natarajan S, Gale B K, Watt R K, et al, Direct Adsorption and Detection of Proteins, Including Ferritin, onto Microlens Array Patterned Bioarrays. Journal of the American Chemical Society. 2007; 129(30):9252-3.
43. Chang-Yen D A, Myszka D, Gale B K A. A novel PDMS microfluidic spotter for fabrication of protein chips and microarrays. Proc SPIE. 2005; 5718:111.
44. Natarajan S, Hatch A, Myszka D G, Gale B K. Optimal Conditions for Protein Array Deposition Using Continuous Flow. Anal Chem. 2008; 80:8561-7.
45. Eddings M Aea. Improved continuous-flow print head for micro-array deposition Anal Biochem. 2008; 387:55-9.
46. Grunwell J R, Glass Lacoste T D, Deniz A A, Chemla D S, Schultz P G. Monitoring the Conformational Fluctuations of DNA Hairpins Using Single-Pair Fluorescence Resonance Energy Transfer. Journal of the American Chemical Society. 2001; 123(18):4295-303.
47. Wennmalm S, Edman L, Rigler R, Conformational fluctuations in single DNA molecules. Proceedings of the National Academy of Sciences of the United States of America. 1997; 94(20):10641-6.
48. Ladd J, Boozer C, Yu Q, Chen S, Homola J, Jiang S. DNA-Directed Protein Immobilization on Mixed Self-Assembled Monolayers via a Streptavidin Bridge. Langmuir. 2004; 20(19):8090-5.
49. Esseghaier C, Helali S, Ben Fredj H, Tlili A, Abdelghani A. Polypyrrole-neutravidin layer for impedimetric biosensor. Sensors and Actuators, B: Chemical. 2008, B131 (2):584-9.
50. Sun H, Choy T S, Zhu D R, Yarn W C, Fu Y S. Nano-silver-modified PQC/DNA biosensor for detecting E. coli in environmental water. Biosensors & Bioelectronics. 2009; 24(5):1405-10.
51. Hall W P, Ngatia S N, Van Duyne R P. LSPR Biosensor Signal Enhancement Using Nanoparticle-Antibody Conjugates. Journal of Physical Chemistry C. 2011; 115(5): 1410-4.
52. Bashir R, Gomez R, Sarikaya A Ladisch M R, Sturgis J, Robinson J P, Adsorption of avidin on microfabricated surfaces for protein biochip applications. Biotechnology and Bioengineering. 2001; 73(4):324-8.
53. Lanka O, Del Campo F J, Munoz T X. Pathogen detection: A perspective of traditional methods and biosensors. Biosensors & Bioelectronics. 2007:22(7):1205-17.
54. Barton A C, Davis F, Higson S P J. Labeless Immunosensor Assay for the Stroke Marker Protein Neuron Specific Enolase Based upon an Alternating Current Impedance Protocol. Analytical Chemistry (Washington, D.C., United States). 2008; 80(24)9411-6.
55. Zhavnerko G K, Yi S J, Chung S H, Yuk J S, Ha K S. Oriented immobilization of C-reactive protein on solid surface for biosensor applications. NATO Science Series, II: Mathematics, Physics and Chemistry. 2004; 152(Frontiers of Multifunctional Integrated Nanosystems):95-108.
56. Cooper M A. Optical biosensors in drug discovery. Nature Reviews Drug Discovery. 2002, 1(7):515-28.
57. Teeter J S, Meyerhoff R D. Environmental fate and chemistry of raloxifene hydrochloride. Environmental Toxicology and Chemistry. 2002, 21(4):729-36.
58. Barrett-Connor E, Mosca L, Collins P, Geiger M J, Grady D, Kornitzer M, et al. Effects of Raloxifene on Cardiovascular Events and Breast Cancer in Postmenopausal Women. New England Journal of Medicine. 2006; 355(2):125-37.
59. Dodge J A, Lugar C W, Cho S, Short L L, Sato M, Yang N N, et al. Evaluation of the major metabolites of raloxifene as modulators of tissue selectivity. The Journal of Steroid Biochemistry and Molecular Biology. 1997; 61(1-2):97-106.
60. Dutertre M, Smith C L. Molecular Mechanisms of Selective Estrogen Receptor Modulator (SERM) Action. Journal of Pharmacology and Experimental Therapeutics. 2000; 295(2):431-7.
61. Morello K C, Wurz G T, DeGregorio M W. Pharmacokinetics of Selective Estrogen Receptor Modulators. Clinical Pharmacokinetics. 2003; 42(4):361-72.
62. Magde D, Elson E, Webb W W. Thermodynamic fluctations in a reacting system. Measurement by fluorescence correlation spectroscopy. Physical Review Letters. 1972; 29(11):705-8.
63. Koppel D E, Axelrod D, Schlessinger J, Elson E L, Webb W W. Dynamics of fluorescence marker concentration as a probe of mobility. Biophysical Journal, 1976; 16(11): 1315-29.
64. Magde D, Elson E L, Webb W W. Fluorescence correlation spectroscopy, II. Experimental realization. Biopolymers. 1974; 13(1):29-61.
65. Thompson N L, Navaratnarajah P, Wang X. Measuring Surface Binding Thermodynamics and Kinetics by Using Total Internal Reflection with Fluorescence Correlation Spectroscopy: Practical Considerations. Journal of Physical Chemistry B. 2011; 115(1):120-31.
66. Starr T E, Thompson N L. Total internal reflection with fluorescence correlation spectroscopy: combined surface reaction and solution diffusion. Biophysical Journal. 2001; 80(3):1575-84.
67. Hansen R L, Harris J M. Measuring reversible adsorption kinetics of small molecules at solid/liquid interfaces by total internal reflection fluorescence correlation spectroscopy. Anal Chem, 1998; 70(20):4247-56.
68. Thompson N L, Burghardt T P, Axelrod D. Measuring surface dynamics of biomolecules by total internal reflection fluorescence with photobleaching recovery or correlation spectroscopy. Biophysical Journal, 1981; 33(3): 435-54.
69. Maiti S, Haupts U, Webb W W. Fluorescence correlation spectroscopy: diagnostics for sparse molecules. Proceedings of the National Academy of Sciences of the United States of America. 1997; 94(22).11753-7.
70. Watanabe H, Yamaguchi S, Sen S. Morita A, Tahara T. "Half-hydration" at the air/water interface revealed by heterodyne-detected electronic sum frequency generation spectroscopy, polarization second harmonic generation, and molecular dynamics simulation. J Chem Phys. 2010; 132: 144701/1-/9.
71. Golovan Melnikov V A, Bestem'Yanov K P, Zabotnov S V, Gordienko V M, Timoshenko V Y, et al. Disorder-correlated enhancement of second-harmonic generation in strongly photonic porous gallium phosphide. Applied Physics B: Lasers and Optics. 2005; 81(2-3):353-6.
72. Frostell-Karlsson A, Remaeus A. Roos H. Andersson K, Borg P, Haemaelaeinen M, et al. Biosensor Analysis of the Interaction between Immobilized Human Serum Albumin and Drug Compounds for Prediction of Human Serum Albumin Binding Levels. Journal of Medicinal Chemistry. 2000; 43(10).1986-92.
73. Murtaza R, Jackman H L, Alexander B, Lleshi-Tali A, Winnie A P, Igic R. Simultaneous determination of mepivacaine, tetracaine, and p-butylaminobenzoic acid by high-performance liquid chromatography. Journal of Pharmacological and Toxicological Methods. 2001; 46(3): 131-6.
74. Haes A J, Van Duyne R P. A nanoscale optical biosensor: Sensitivity and selectivity of an approach based on the localized surface plasmon resonance spectroscopy of triangular silver nanoparticles. Journal of the American Chemical Society, 2002; 124(35):10596-604.
75. Zhao S, Walker D S, Reichert W M. Cooperativity in the binding of avidin to biotin-lipid-doped Langmuir-Blodgett films. Langmuir. 1993; 9(11):3166-73.
76. Shi J, Yang T, Kataoka S, Zhang Y, Diaz A J, Cremer P S. GM1 Clustering Inhibits Cholera Toxin Binding in Supported Phospholipid Membranes. Journal of the American Chemical Society. 2007; 129(18):5954-61.
77. Pierce Biotechnologies I. [cited]; Available from: http://www.piercenetcom/guide/guide-elisa-substrates.

78. Vornholt W, Hartmann M, Keusgen M. SPR studies of carbohydrate-lectin interactions as useful tool for screening on lectin sources. Biosensors and Bioelectronics. 2007; 22(12):2983-8.
79. Jung H, Yang T, Lasagna M D, Shi J, Reinhart G D, Cremer P S. Impact of hapten presentation on antibody binding at lipid membrane interfaces. Biophysical Journal. 2008; 94(8):3094-103.
80. Sino Biological I.
81. Hirano S-I, Yogo T, Kikuta K-I, Noda K-I, Ichida M, Nakamura A. Synthesis of KTiOPO4 (KTP) thin films using metallo-organics. Journal of the American Ceramic Society. 1995; 78(11):2956-60.
82. Li D, Kong L, Zhang L, Yao X. Sol-gel preparation and characterization of transparent KTiOPO4/SiO2 nanocomposite glass for second harmonic generation. Journal of Non-Crystalline Solids. 2000; 271(1,2):45-55.
83. Polanski M, Anderson N L. A List of Candidate Cancer Biomarkers for Targeted Proteomics. Biomarker Insights. 2006; 1:1-48.
84. Cook G B, Neaman I E, Goldblatt J L, Cambetas D R, Hussain M, Luftner D, et al. Clinical utility of serum HER-2/neu testing on the bayer Immuno 1 automated system in breast cancer. Anticancer Research. 2001; 21(2B):1465-70.
85. Gann P H, Hennekens C H, Stampfer M J. A prospective evaluation of plasma prostate-specific antigen for detection of prostatic cancer. JAMA: the journal of the American Medical Association. 1995; 273(4):289-94.
86. Yamaguchi K, Nagano M. Torada N, Hamasaki N, Kawakita M, Tanaka M. Urine diacetylspermine as a novel tumor marker for pancreatobiliary carcinomas. Rinsho Byori. 2004; 52:336-9.
87. Ciambellotti E, Coda C, Lanza E. Determination++ of CA 15-3 in the control of primary and metastatic breast carcinoma. Minerva Med. 1993; 84(Copyright (C) 2013 U.S. National Library of Medicine.):107-12.
88. Mor G, Visintin I, Lai Y, Zhao H, Schwartz P, Rutherford T, et al. Serum protein markers for early detection of ovarian cancer. Proceedings of the National Academy of Sciences of the United States of America. 2005; 102: 7677-82.
89. Xiao Ying W, Li L, Hu Z, Ma Y, Jiao L, et al. An approach to studying lung cancer-related proteins in human blood. Mol Cell Proteomics. 2005; 4:1480-6.
90. Jemal A, Siegel R, Ward E, Hao Y, Xu J, Murray T, et al. Cancer Statistics, 2008, CA: A Cancer Journal for Clinicians. 2008; 58(2):71-96.
91. Rhea J M, Molinaro R J. Cancer biomarkers: surviving the journey from bench to bedside. MLO: medical laboratory observer. 2011; 43(3):10-2, 6, 8; quiz 20, 2.
92. Polanski M, Anderson N. A list of candidate cancer biomarkers for targeted proteomics. Biomarker Insights. 20071:1-48.
93. Mattson G, Conklin E, Desai S, Nielander G, Savage M D, Morgensen S. A practical approach to crosslinking, Molecular Biology Reports. 1993; 17(3):167-83.
94. Yoshitake S, Imagawa M, Ishikawa E, Niitsu Y, Urushizaki I, Nishiura M, et al. Mild and efficient conjugation of rabbit Fab' and horseradish peroxidase using a maleimide compound and its use for enzyme immunoassay. Journal of Biochemistry. 1982; 92(5):1413-24.
95. Liu J, Eddings M A, Miles A R, Bukasov R, Gale B K, Shumaker-Parry J S. In situ microarray fabrication and analysis using a microfluidic flow cell array integrated with surface plasmon resonance microscopy. Anal Chem. 2009; 81:4296-301.
96. Natarajan S. Hatch A, Myszka David G, Gale Bruce K. Optimal conditions for protein array deposition using continuous flow. Anal Chem. 2008; 80(22):8561-7.

We claim:
1. A method of detecting an analyte of interest comprising
a) introducing a sample comprising an analyte of interest to an antibody or antibody fragment;
b) incubating the sample and antibody or antibody fragment under conditions sufficient to allow binding of the analyte of interest to the antibody or antibody fragment; and
c) detecting the binding of the analyte of interest to the antibody or antibody fragment using a coherent label-free second harmonic direct detection system, wherein the coherent label-free second harmonic direct detection system comprises a detection assembly, wherein the detection assembly comprises a sensor having a first surface that produces emitted light from a substrate assembly, wherein the light from the first surface of the sensor is optically heterodyned to amplify the second harmonic signal, wherein the first surface of the sensor is covered with a non-linear optically-active surface layer, and wherein the non-linear optically-active surface layer is covered with a silicon oxide sol-gel film to create a self-contained heterodyne optical arrangement.
2. The method of claim 1, wherein the analyte of interest is a protein, nucleic acid, small molecule, or fragment thereof.
3. The method of claim 1, wherein the sample is a biological sample.
4. The method of claim 3, wherein the biological sample is selected from blood, serum, urine, milk, cell lysate, and tissue lysate.
5. The method of claim 1, wherein the antibody or antibody fragment is immobilized on a support.
6. The method of claim 1, wherein the antibody or antibody fragment is known to bind the analyte of interest.
7. The method of claim 1, wherein the concentration of the analyte in the sample is sub-femtomolar or greater.
8. The method of claim 1, wherein detecting the binding of the analyte of interest to the antibody or antibody fragment using the coherent label-free second harmonic detection system comprises using second harmonic imaging (SHI) to detect the binding of the analyte of interest.
9. The method of claim 8, wherein detecting the binding of the analyte of interest to the antibody or antibody fragment using the coherent label-free second harmonic detection system further comprises determining binding properties of the analyte of interest using second-harmonic correlation spectroscopy.
10. The method of claim 9, wherein detecting the binding of the analyte of interest to the antibody or antibody fragment using the coherent label-free second harmonic detection system comprises:
a) using second-harmonic correlation spectroscopy to determine binding affinity data for the analyte of interest based upon a single measured concentration of the analyte of interest; and
b) using second-harmonic imaging to quantify the analyte of interest.
11. The method of claim 8, wherein the coherent label-free second harmonic detection system further comprises:
a) a laser that generates incident light at a first frequency; wherein the substrate assembly has an optical prism and a support layer that supports the sample and antibody or antibody fragment between the support layer and the prism, wherein the substrate receives incident light at the first frequency from the laser; and wherein the detection assembly receives emitted light from the substrate assembly, wherein the detection assembly detects a second harmonic signal corresponding to emitted light having a second frequency equal to twice the first frequency; and b) a processing assembly that receives the second harmonic signal and determines a quantity of the analyte of interest.

\* \* \* \* \*